US012773327B2

(12) United States Patent
Flores et al.

(10) Patent No.: US 12,773,327 B2
(45) Date of Patent: Oct. 27, 2026

(54) ADDITIVE MANUFACTURING TECHNIQUES FOR A SOCKET AND LINER COMBINATION DEVICE

(71) Applicant: Hanger, Inc., Austin, TX (US)

(72) Inventors: Aaron Flores, Austin, TX (US); Justin Mieth, Austin, TX (US); Antonio Dias, Scottsdale, AZ (US); Ryan Kleppe, Austin, TX (US)

(73) Assignee: Hanger, Inc., Austin, TX (US)

( * ) Notice: Subject to any disclaimer, the term of this patent is extended or adjusted under 35 U.S.C. 154(b) by 0 days.

(21) Appl. No.: 18/852,840

(22) PCT Filed: Nov. 6, 2023

(86) PCT No.: PCT/US2023/036863

§ 371 (c)(1),
(2) Date: Sep. 30, 2024

(87) PCT Pub. No.: WO2024/102333

PCT Pub. Date: May 16, 2024

(65) Prior Publication Data

US 2025/0255737 A1 Aug. 14, 2025

Related U.S. Application Data

(60) Provisional application No. 63/423,311, filed on Nov. 7, 2022.

(51) Int. Cl.

*A61F 2/78* (2006.01)
*A61F 2/54* (2006.01)

(Continued)

(52) U.S. Cl.

CPC .............. *A61F 2/7812* (2013.01); *A61F 2/54* (2013.01); *A61F 2/60* (2013.01); *A61F 2/80* (2013.01);

(Continued)

(58) Field of Classification Search

CPC ...... A61F 2/80; A61F 2/78; A61F 2/76; A61F 2/70; A61F 2/60; A61F 2/54;

(Continued)

(56) References Cited

U.S. PATENT DOCUMENTS

| | | | |
|---|---|---|---|
| 667,534 | A | 2/1901 | Kimball |
| 2,790,254 | A | 4/1957 | Burns |

(Continued)

FOREIGN PATENT DOCUMENTS

| | | |
|---|---|---|
| BR | 112018004850 | 8/2023 |
| CA | 2664803 | 4/2008 |

(Continued)

OTHER PUBLICATIONS

Translation of WO2020069817A1 Bause. (Year: 2020).*

(Continued)

*Primary Examiner* — Christie Bahena
(74) *Attorney, Agent, or Firm* — Foley & Lardner LLP

(57) ABSTRACT

A prosthetic assembly includes a socket and a liner. The socket includes a first interlocking feature and defines an inner volume. The liner includes a second interlocking feature. The first interlocking feature and the second interlocking feature are configured to engage each other when the liner is inserted into the inner volume of the socket. The liner is configured to receive a distal limb of a patient. At least one of the socket or the liner include inner voids extending within walls of the socket or the liner.

18 Claims, 17 Drawing Sheets

(51) Int. Cl.
*A61F 2/60* (2006.01)
*A61F 2/80* (2006.01)
*B33Y 80/00* (2015.01)

(52) U.S. Cl.
CPC ....... *A61F 2002/7837* (2013.01); *B33Y 80/00* (2014.12)

(58) Field of Classification Search
CPC ........ A61F 2/7812; A61F 2/72; A61F 2/5044; A61F 2002/5044; A61F 2002/5046; A61F 2002/5052; A61F 2002/5053; A61F 2002/5058; A61F 2002/7615; A61F 2002/802; A61F 2002/807; B33Y 80/00
See application file for complete search history.

(56) References Cited

U.S. PATENT DOCUMENTS

| | | | | |
|---|---|---|---|---|
| 3,490,078 | A | 1/1970 | Perez, Jr. | |
| 4,134,159 | A | 1/1979 | Wilson | |
| 4,283,800 | A | 8/1981 | Wilson | |
| 4,702,255 | A | 10/1987 | Schenkl | |
| 5,458,657 | A | 10/1995 | Rasmusson | |
| 5,653,766 | A | 8/1997 | Naser | |
| 6,428,494 | B1 | 8/2002 | Schwenn et al. | |
| 6,605,118 | B2 | 8/2003 | Capper et al. | |
| 6,669,736 | B2 | 12/2003 | Slemker et al. | |
| 7,162,075 | B2 | 1/2007 | Littlefield et al. | |
| 7,227,979 | B2 | 6/2007 | Littlefield et al. | |
| 7,242,798 | B2 | 7/2007 | Littlefield et al. | |
| 7,356,379 | B2 | 4/2008 | Slemker et al. | |
| 8,838,263 | B2 | 9/2014 | Sivak et al. | |
| 9,161,848 | B2 | 10/2015 | Tompkins | |
| 9,232,827 | B1 | 1/2016 | Penn | |
| 9,402,760 | B2 | 8/2016 | Gordon et al. | |
| 9,469,075 | B2 | 10/2016 | Zachariasen et al. | |
| 9,480,581 | B2 | 11/2016 | Layman et al. | |
| 9,486,334 | B2 | 11/2016 | Tompkins | |
| 9,610,731 | B2 | 4/2017 | Zachariasen | |
| 9,738,036 | B2 | 8/2017 | Littlefield | |
| 9,873,229 | B2 | 1/2018 | Chun et al. | |
| 9,908,295 | B2 | 3/2018 | Ou et al. | |
| 9,987,801 | B2 | 6/2018 | Littlefield | |
| 10,010,433 | B2 | 7/2018 | Layman et al. | |
| 10,089,662 | B2 | 10/2018 | Norman | |
| 10,238,511 | B1 | 3/2019 | Newton et al. | |
| 10,241,498 | B1 | 3/2019 | Beard et al. | |
| 10,357,383 | B2 | 7/2019 | Tompkins | |
| 10,463,525 | B2 | 11/2019 | Littlefield et al. | |
| 10,517,746 | B2 | 12/2019 | Bernhardt et al. | |
| 10,528,032 | B2 | 1/2020 | Schouwenburg et al. | |
| 10,561,521 | B2 | 2/2020 | Littlefield et al. | |
| 10,603,203 | B2 | 3/2020 | Littlefield et al. | |
| 10,624,767 | B2 | 4/2020 | Jonsson et al. | |
| 10,639,173 | B2 * | 5/2020 | Walter | A61F 2/78 |
| 10,682,846 | B2 | 6/2020 | Littlefield et al. | |
| 10,695,211 | B2 | 6/2020 | Mottram et al. | |
| 10,703,084 | B2 | 7/2020 | Littlefield et al. | |
| 10,710,356 | B2 | 7/2020 | Littlefield et al. | |
| 10,726,617 | B2 | 7/2020 | Littlefield et al. | |
| 10,766,246 | B2 | 9/2020 | Nauka et al. | |
| 10,846,925 | B2 | 11/2020 | Littlefield et al. | |
| 10,905,568 | B2 | 2/2021 | Erenstone | |
| 11,086,148 | B2 | 8/2021 | Chumbley et al. | |
| D943,753 | S | 2/2022 | Grygar | |
| 2004/0068337 | A1 | 4/2004 | Watson et al. | |
| 2004/0260402 | A1 | 12/2004 | Baldini et al. | |
| 2005/0038522 | A1 | 2/2005 | Helenberger et al. | |
| 2006/0094951 | A1 | 5/2006 | Dean et al. | |
| 2007/0055383 | A1* | 3/2007 | King | A61F 2/70 623/34 |
| 2007/0081717 | A1 | 4/2007 | Littlefield | |
| 2007/0213839 | A1 | 9/2007 | Nachbar | |
| 2007/0225824 | A1* | 9/2007 | Einarsson | A61F 2/78 623/36 |
| 2007/0265727 | A1 | 11/2007 | Bae et al. | |
| 2009/0132056 | A1* | 5/2009 | Kania | A61F 2/7812 623/36 |
| 2012/0143351 | A1* | 6/2012 | Tompkins | A61B 5/1123 623/34 |
| 2013/0046394 | A1* | 2/2013 | Lipschutz | A61F 2/72 623/25 |
| 2013/0274896 | A1* | 10/2013 | Wang | A61F 7/007 623/36 |
| 2014/0379097 | A1 | 12/2014 | Hurley et al. | |
| 2015/0018974 | A1 | 1/2015 | Dillingham | |
| 2015/0105867 | A1 | 4/2015 | Novak | |
| 2015/0142150 | A1 | 5/2015 | Layman et al. | |
| 2015/0250715 | A1 | 9/2015 | Adams et al. | |
| 2015/0265434 | A1 | 9/2015 | Hurley et al. | |
| 2016/0074182 | A1 | 3/2016 | Celebi et al. | |
| 2016/0184113 | A1* | 6/2016 | Koniuk | A61F 2/7812 623/33 |
| 2016/0287425 | A1 | 10/2016 | Gilmer et al. | |
| 2017/0318900 | A1 | 11/2017 | Charlesworth et al. | |
| 2018/0281312 | A1 | 10/2018 | Littlefield et al. | |
| 2018/0353308 | A1 | 12/2018 | Tompkins | |
| 2019/0015238 | A1 | 1/2019 | Mottram et al. | |
| 2019/0125554 | A1 | 5/2019 | Kramer et al. | |
| 2019/0183663 | A1 | 6/2019 | Will et al. | |
| 2019/0298553 | A1* | 10/2019 | Gibbard | A61F 2/7812 |
| 2020/0188141 | A1 | 6/2020 | Muller | |
| 2021/0024775 | A1 | 1/2021 | Rolland et al. | |
| 2021/0137708 | A1* | 5/2021 | Orrason | A61F 2/7812 |
| 2021/0145613 | A1 | 5/2021 | Anderson et al. | |
| 2021/0275326 | A1 | 9/2021 | Dechev et al. | |
| 2021/0322200 | A1 | 10/2021 | Goodnough | |
| 2021/0338459 | A1 | 11/2021 | Tompkins et al. | |
| 2021/0401596 | A1 | 12/2021 | Hunter et al. | |
| 2022/0175571 | A1 | 6/2022 | Goodnough | |
| 2022/0183861 | A1 | 6/2022 | Flores et al. | |
| 2022/0211522 | A1 | 7/2022 | Polta et al. | |
| 2023/0149201 | A1 | 5/2023 | Smith et al. | |
| 2024/0148525 | A1 | 5/2024 | Koppe et al. | |
| 2024/0325174 | A1 | 10/2024 | Polta et al. | |

FOREIGN PATENT DOCUMENTS

| | | | | |
|---|---|---|---|---|
| CA | 3171895 | | 9/2019 | |
| CN | 102209965 | | 10/2011 | |
| CN | 106537410 | | 3/2017 | |
| CZ | 2022189 | | 11/2023 | |
| DE | 10 2010 019 843 | A1 | 11/2011 | |
| DE | 10 2018 133 486 | A1 | 6/2020 | |
| EP | 2 735 290 | A1 | 5/2014 | |
| EP | 3 815 650 | A1 | 5/2021 | |
| GB | 2 103 490 | A | 8/1984 | |
| JP | 2023-094208 | | 7/2023 | |
| KR | 101675400 | | 11/2016 | |
| KR | 20180127120 | | 11/2018 | |
| WO | WO-94/04102 | A1 | 3/1994 | |
| WO | WO-9840038 | A1 * | 9/1998 | A61F 2/76 |
| WO | WO-2013/142343 | A1 | 9/2013 | |
| WO | WO-2014/113581 | | 7/2014 | |
| WO | WO-2014130878 | A1 * | 8/2014 | A61F 2/80 |
| WO | WO-2015073793 | A1 * | 5/2015 | A61F 2/80 |
| WO | WO-2017/042550 | A1 | 3/2017 | |
| WO | WO-2017/151577 | A1 | 9/2017 | |
| WO | WO-2018/115874 | A1 | 6/2018 | |
| WO | WO-2019/178686 | A1 | 9/2019 | |
| WO | WO-2020069817 | A1 * | 4/2020 | B33Y 80/00 |
| WO | WO-2022/091453 | | 5/2022 | |

OTHER PUBLICATIONS

International Search Report and Written Opinion regarding PCT Application No. PCT/US2023/036863, dated Mar. 15, 2024, 17 pages.

Davies, S., "HP 3D printing tech & nTopology Design software enables prosthetic device manufacture in Guatemala." Oct. 13, 2021, 3D Printing and Additive Manufacturing Intelligence.

(56) References Cited

OTHER PUBLICATIONS

Fairley, Miki. "3D Printing Gains Momentum in Clinical O&P." The O&P Edge Magazine, Jan. 3, 2022, opedge.com/3d-printing-gains-momentum-in-clinical-op/.
International Search Report and Written Opinion for International Application No. PCT/US2017/015981, mail date May 11, 2017, 14 pages.
International Search Report and Written Opinion issued on PCT/US2023/032048 dated Mar. 13, 2024.
Rogers, B. "Advanced trans-tibial socket fabrication using selective laser sintering." Prosthetics and Orthotics International. Mar. 2007, No. 31, pp. 88-100.
Extended European Search Report issued on EP23863740.9 dated Nov. 12, 2025.
Extended European Search Report for Application No. 23889371.3 mailing date Feb. 5, 2026, 11 pages.

* cited by examiner

ADDITIVE MANUFACTURING TECHNIQUES FOR A SOCKET AND LINER COMBINATION DEVICE

CROSS-REFERENCE TO RELATED PATENT APPLICATION

This PCT application claims the benefit of and priority to U.S. Provisional Application No. 63/423,311, filed Nov. 7, 2022, the entire disclosure of which is incorporated by reference herein.

BACKGROUND

The present disclosure relates generally to prosthetics and orthotics. More particularly, the present disclosure relates to additive manufacturing of protective devices, prosthetics and/or orthotics.

SUMMARY

One implementation of the present disclosure is a prosthetic assembly, according to some embodiments. In some embodiments, the prosthetic assembly includes a socket and a liner. In some embodiments, the socket includes a first interlocking feature and defines an inner volume. In some embodiments, the liner includes a second interlocking feature. In some embodiments, the first interlocking feature and the second interlocking feature are configured to engage each other when the liner is inserted into the inner volume of the socket. In some embodiments, the liner is configured to receive a distal limb of a patient. In some embodiments, at least one of the socket or the liner include inner voids extending within walls of the socket or the liner.

In some embodiments, the inner voids include a first set of internal channels for heat dissipation from the patient's distal limb to facilitate cooling of the patient's distal limb. In some embodiments, the inner voids include a second set of internal channels for moisture evaporation from the patient's distal limb to facilitate evaporation of sweat or bodily fluids from the patient's distal limb. In some embodiments, the inner voids include a third set of internal channels for electrical components. In some embodiments, the third set of internal channels are configured to receive at least one sensor or transducer and at least one myoelectric wire. In some embodiments, the electrical components include components of a Peltier cooling system. In some embodiments, the inner voids include a fourth set of internal channels configured to provide therapy or medication to the patient's distal limb.

In some embodiments, at least one of the socket or the liner includes a variable thickness along a longitudinal length or radial direction of the socket or the liner. In some embodiments, the liner includes a lattice structure. In some embodiments, the lattice structure is positioned at a distal end of the liner and positioned between a double wall of the liner. In some embodiments, the lattice structure is configured to facilitate desired transfer of forces between the prosthetic assembly and the patient's distal limb, to absorb impact forces, and to reduce shear stress.

In some embodiments, the prosthetic assembly is an above-the-knee or below-the-knee lower limb prosthetic assembly. In some embodiments, the prosthetic assembly is an above-the-elbow, below-the-elbow, at the wrist, or a finger upper limb prosthetic assembly.

In some embodiments, the socket is manufactured from a thermoplastic or a thermoplastic reinforced with high strength material. In some embodiments, the liner is manufactured from a flexible silicone material or a higher durometer rubber. In some embodiments, an exterior surface of the liner and an internal surface of the socket are configured to engage each other to define sealed vacuum sections between the liner and the socket. In some embodiments, other sections of the liner and the socket do not define sealed vacuum sections.

In some embodiments, the prosthetic assembly is entirely manufactured through at least one of additive manufacturing or injection molding. In some embodiments, at least one of the liner or the socket include connection points configured to couple additional componentry to the prosthetic assembly. In some embodiments, the connection points include an extrusion or a recess disposed on the liner or the socket.

In some embodiments, the first interlocking feature is a protrusion and the second interlocking feature is a void. In some embodiments, the protrusion is configured to be received within the void to removably couple the socket with the liner.

In some embodiments, the first interlocking feature is a void and the second interlocking feature is a protrusion. In some embodiments, the protrusion is configured to be received within the void to removably couple the socket with the liner. In some embodiments, the socket and the liner conform to an anatomical shape of the patient's distal limb.

Another implementation of the present disclosure is a method for manufacturing a prosthetic assembly that includes a socket and a liner, according to some embodiments. In some embodiments, the method includes using a digital scanner to capture an anatomical structure of a patient's distal limb, an anatomical structure of a cast of the patient's distal limb, or an anatomical structure of a mold of the patient's distal limb to generate a scan file. In some embodiments, the method includes converting the scan file to a design file. In some embodiments, the method includes modifying the design file to generate a model of the liner and a model of the socket. In some embodiments, the model of the liner and the model of the socket include interlocking features. In some embodiments, the liner is configured to be received within the socket. In some embodiments, the method includes manufacturing the design file to produce the liner and the socket of the prosthetic assembly using at least one of an additive manufacturing process using an additive manufacturing device or an injection molding process.

In some embodiments, modifying the design file includes using build-ups, reductions, or other adjustment to generate the model of the liner and the model of the socket. In some embodiments, modifying the design file further includes designing at least one of the model of the liner or the model of the socket to include inner voids extending within walls of the model of the socket or the model of the liner.

In some embodiments, the inner voids include a first set of internal channels for heat dissipation from the patient's distal limb to facilitate cooling of the patient's distal limb. In some embodiments, the inner voids include a second set of internal channels for moisture evaporation from the patient's distal limb to facilitate evaporation of sweat or bodily fluids from the patient's distal limb. In some embodiments, the inner voids include a third set of internal channels for electrical components. In some embodiments, the third set of internal channels are configured to receive at least one sensor or transducer and at least one myoelectric wire. In some embodiments, the electrical components include components of a Peltier cooling system. In some embodiments, the inner voids include a fourth set of internal channels configured to provide therapy or medication to the patient's distal limb.

In some embodiments, modifying the design file includes adjusting a thickness of the model of the socket or the model of the liner. In some embodiments, the thickness of at least one of the socket or the liner is variable along a longitudinal length or radial direction of the socket or the liner.

In some embodiments, modifying the design file further includes building a lattice structure on the model of the liner. In some embodiments, the lattice structure is positioned at a distal end of the liner and positioned between a double wall of the liner. In some embodiments, the lattice structure is configured to facilitate desired transfer of forces between the prosthetic assembly and the patient's distal limb, to absorb impact forces, and to reduce shear stress.

In some embodiments, the prosthetic assembly is an above-the-knee or below-the-knee lower limb prosthetic assembly. In some embodiments, the prosthetic assembly is an above-the-elbow, below-the-elbow, at the wrist, or a finger upper limb prosthetic assembly.

In some embodiments, manufacturing the socket includes using a thermoplastic or a thermoplastic reinforced with high strength material to fabricate the socket. In some embodiments, manufacturing the liner includes using a flexible silicone material or a higher durometer rubber to fabricate the liner.

In some embodiments, an exterior surface of the liner and an internal surface of the socket are configured to engage each other to define sealed vacuum sections between the liner and the socket. In some embodiments, other sections of the liner and the socket do not define sealed vacuum sections.

In some embodiments, the prosthetic assembly is entirely manufactured through at least one of additive manufacturing or injection molding. In some embodiments, at least one of the liner or the socket include connection points configured to couple additional componentry to the prosthetic assembly.

In some embodiments, the connection points include an extrusion or a recess disposed on the liner or the socket. In some embodiments, the interlocking features include a protrusion and a void. In some embodiments, the protrusion is configured to be received within the void to removably couple the socket with the liner. In some embodiments, the socket and the liner conform to an anatomical shape of the patient's distal limb.

In some embodiments, converting the scan file to the design file includes converting the scan file to a computer assisted design (CAD) or computer assisted manufacturing (CAM) model. In some embodiments, the method further includes uploading design file to a 3D printer. In some embodiments, the socket and the liner of the prosthetic assembly are custom made based on anatomy, requests, and needs for the patient.

In some embodiments, the method further includes assembling the liner and the socket of the prosthetic assembly. In some embodiments, the liner and the socket of the prosthetic assembly are configured to undergo minor shape adjustments without sustaining structural damage.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
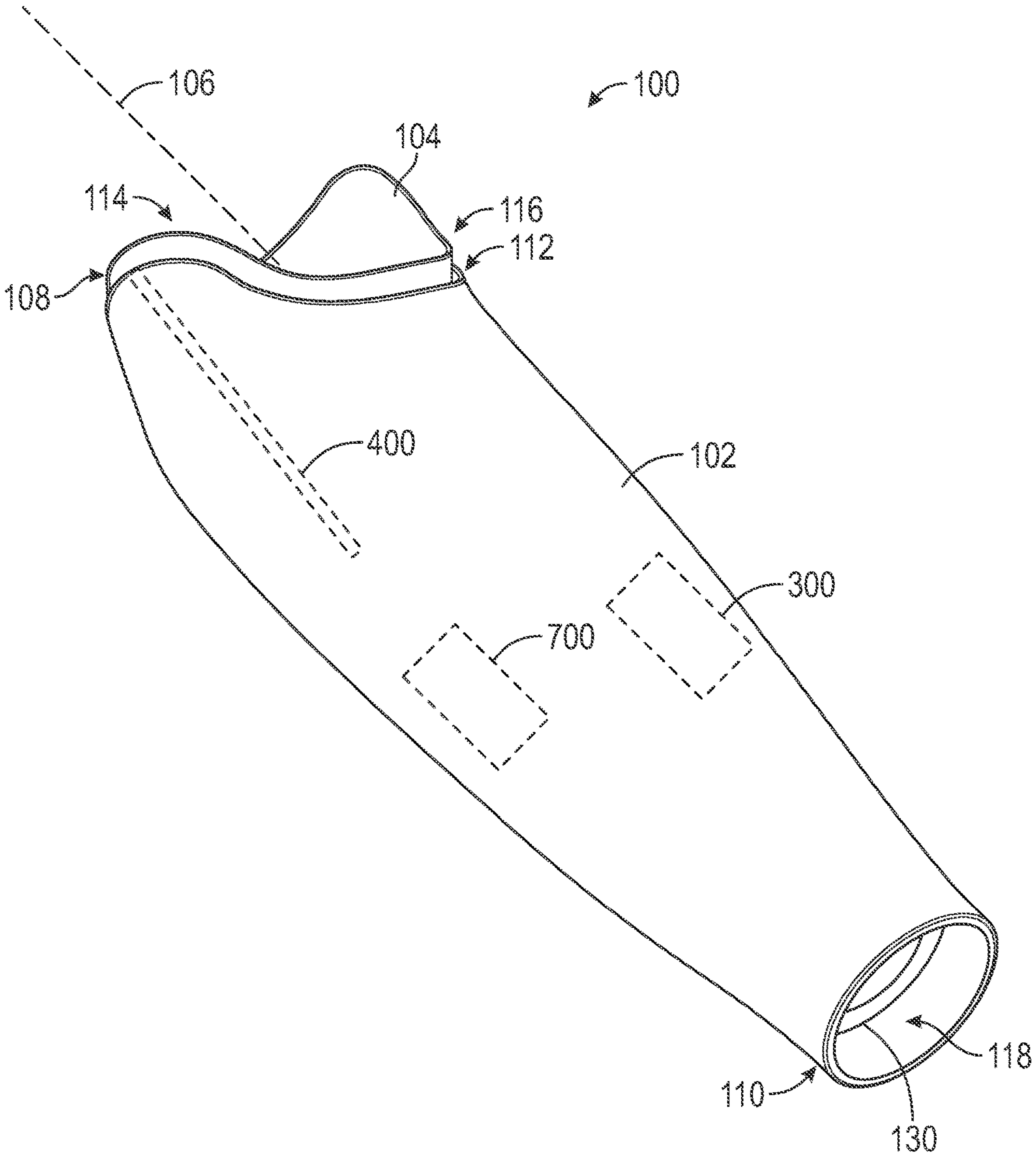
FIG. 1 is a perspective view of an upper limb prosthetic socket and an interfacing liner, according to some embodiments.

Before turning to the FIGURES, which illustrate the exemplary embodiments in detail, it should be understood that the present application is not limited to the details or methodology set forth in the description or illustrated in the FIGURES. It should also be understood that the terminology is for the purpose of description only and should not be regarded as limiting.

Overview

Referring generally to the FIGURES, an upper or lower limb prosthetic socket may be additively manufactured in combination with a corresponding interfacing liner device. In some embodiments, the socket and the liner cooperatively define a combination device and are configured to interlock with each other (e.g., selectably or upon insertion of a patient's distal limb with the liner placed over the patient's distal upper or lower limb). In some embodiments, an entirety of the combination device is additively manufactured (e.g., by a 3D printer) using a layer-by-layer process. In some embodiments, one or more components of the combination device are manufactured by an injection molding process. In some embodiments, a system of strategically placed cutouts and/or extrusions between the socket and the liner overlap so that the socket and the liner interlock or couple with each other.

The combination device may be used for either lower extremity or upper extremity patients and may include one or more attachment points or external receiving members configured to couple external componentry with the socket and/or the liner. In some embodiments, one or more channels, voids, depressions, openings, apertures, grooves, etc., are formed in the liner or the socket to facilitate venting and/or heat dispersion thereby resulting in improved comfortability for the patient. For example, the combination device can include channels that are configured to extend along a path such that gravity may facilitate drawing moisture away from the patient's limb and allowing evaporation of the moisture (e.g., sweat or other bodily fluids) into an external environment. Advantageously, these channels may reduce sweat buildup in the bottom of the socket which improves comfortability of the combination device relative to other prosthetic sockets that do not include venting for moisture. The liner may include a lattice structure positioned according to needs of the patient to absorb impact forces and properly distribute forces on the patient's residual or distal limb.

The techniques described herein for additive manufacturing can additionally be used to manufacture the prosthetic, orthotic, connection insert, or related medical devices as described in U.S. Patent Application Pub. No.: 2018/0353308 A1, filed Jul. 31, 2018, the entire disclosure of which is incorporated by reference herein. Further, any of the additive manufacturing techniques as described in U.S. Patent Application Pub. No.: 2018/0353308 A1 may be used to manufacture any of the devices described herein.

In some embodiments, the prosthetic, orthotic, connection insert, protective device, etc., as described herein are manufactured using any of the techniques as described in U.S. Pat. No. 10,766,246 B2, filed Dec. 15, 2014, the entire disclosure of which is incorporated by reference herein.

Upper Extremity Prosthetic Socket

Figure 2:
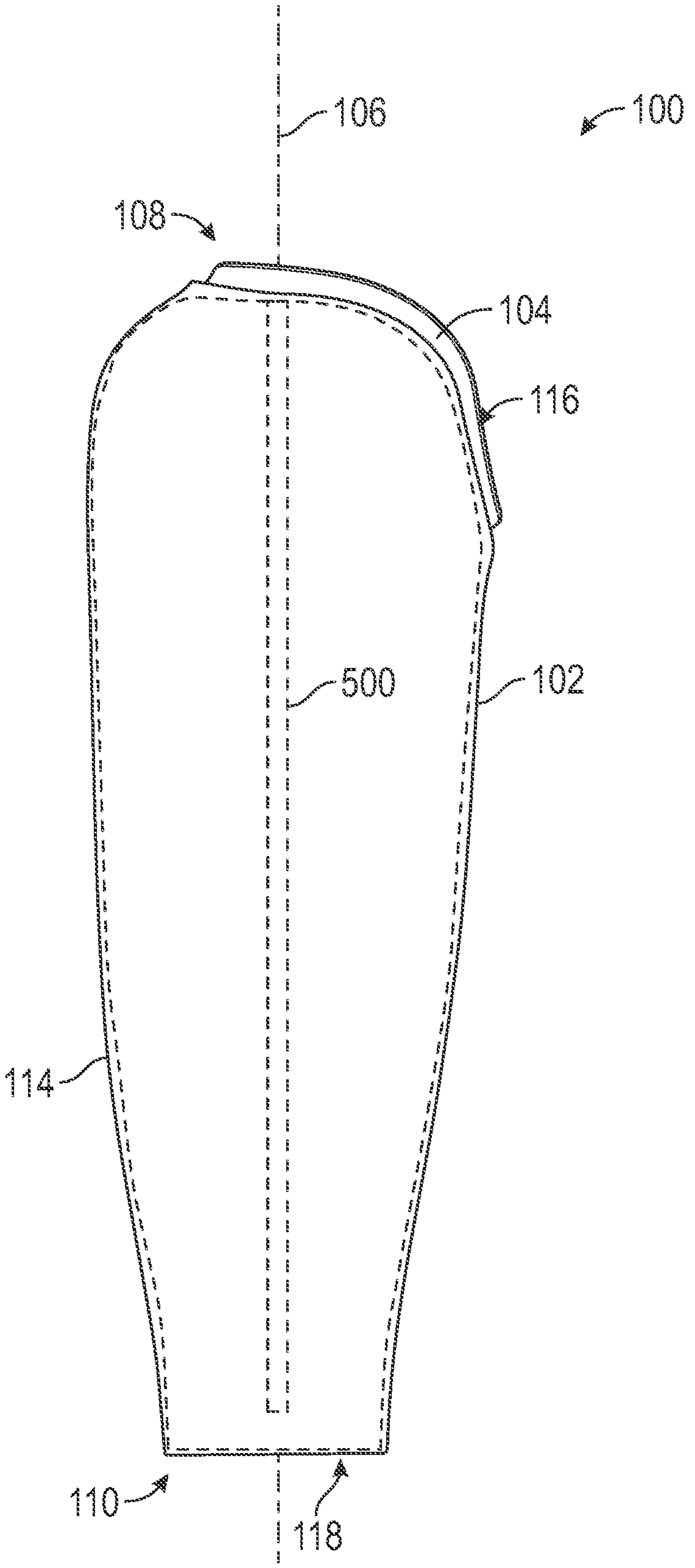
FIG. 2 is a side view of the prosthetic socket and interfacing liner of FIG. 1, according to some embodiments.
Figure 3:
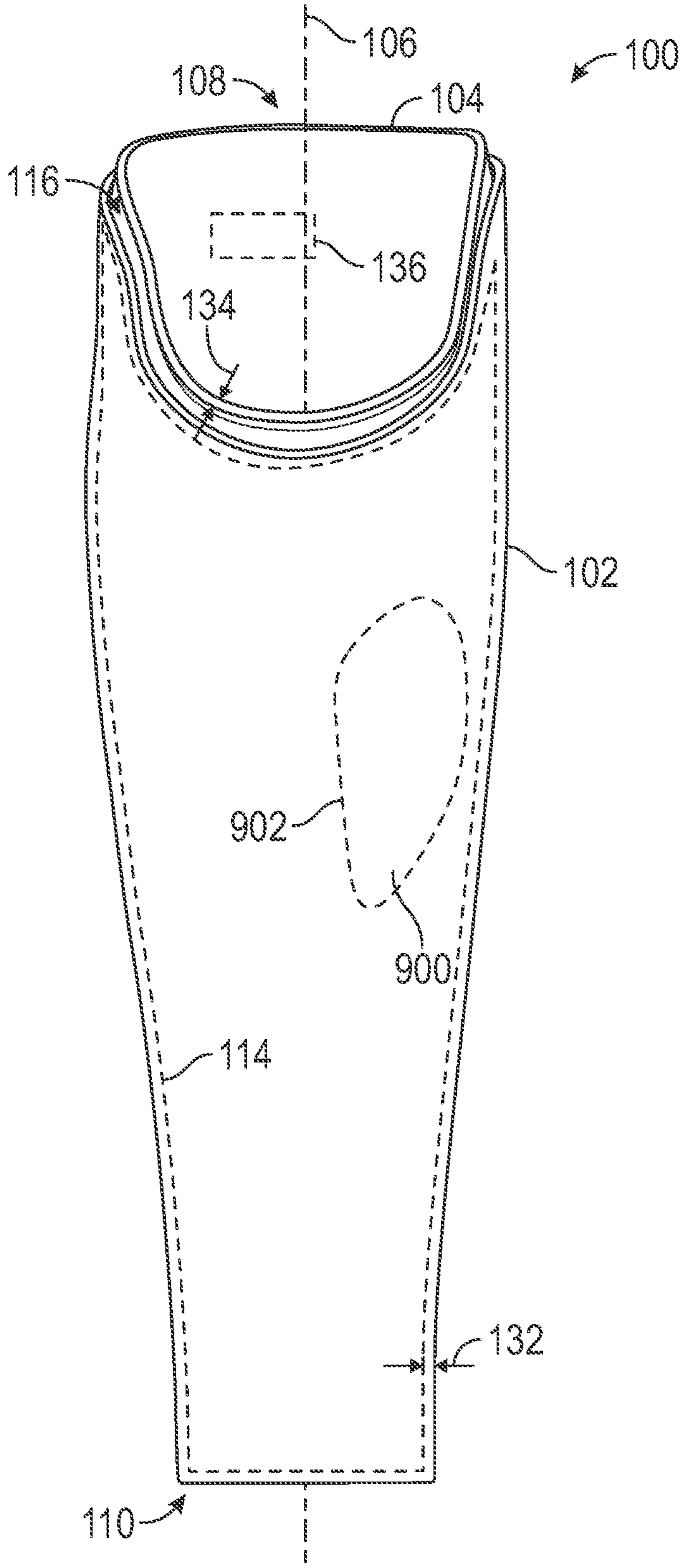
FIG. 3 is a front view of the prosthetic socket and interfacing liner of FIG. 1, according to some embodiments.

Referring to FIGS. 1-3, a prosthetic assembly, a prosthetic device assembly, an upper extremity prosthetic socket assembly, a combination device, etc., shown as upper extremity combination device 100 includes a socket 102 (e.g., an external device, an exterior device, a shell, etc.) and a liner 104 (e.g., an internal device, an interior device, a sleeve, a limb contacting device, etc.). The socket 102 includes or defines a first end 108 and a second end 110. The socket 102 also defines an inner volume 114 (e.g., an interior, a compartment, a void, etc.) that is configured to receive the liner 104. The socket 102 may include a first opening 116 at the first end 108 into which the liner 104 may be inserted and a second opening 118 at the second end 110. In some embodiments, the first opening 116 is configured to provide an open end of the socket 102 so that the user can insert their distal upper limb (with the liner 104 installed onto the user's distal upper limb). In some embodiments, the second opening 118 is smaller in size than the first opening 116. In some embodiments, the socket 102 includes connection structure 130 (e.g., threads, interlocking members, openings, recesses, annular grooves, an adapter, a mount, etc.) that are positioned at the second end 110 and configured to couple (e.g., threadingly, interlockingly, slip fit, press fit, via fasteners, etc.) with an attachable or external componentry. In some embodiments, the connection structure 130 is disposed on the liner 104 so that the attachable or external componentry can be coupled with the liner 104. In some embodiments, the liner 104 is configured to directly couple, abut, contact, seal with, engage, etc., the patient's distal upper limb (e.g., along inner surfaces of the liner 104). In some embodiments, an exterior surface of the liner 104 is configured to directly couple, abut, contact, interlock with, seal with, engage, etc., an interior surface of the socket 102. In some embodiments, the liner 104 is configured to releasably couple with the socket 102 through interlocking features 300.

The combination device 100 may be an above the elbow or a below the elbow prosthetic assembly. The socket 102 and the liner 104 may have contours or geometry that substantially matches the contours and geometry of the patient's residual limb. The liner 104 and the socket 102 may be configured to surround, enclose, or fully receive the patient's residual limb. In some embodiments, structural contours of the liner 104 and the socket 102 on either exterior or interior surfaces of the liner 104 and the socket 102 match or correspond with anatomical contours of the patient's residual limb (e.g., the patient's residual upper limb, or the patients residual lower limb in the case of the combination device 200 described below). In some embodiments, the socket 102 is configured to provide proper distribution of forces across the patient's residual or distal limb. In some embodiments, an entirety of the components of the combination device 100 are manufactured through additive manufacturing.

In some embodiments, the combination device 100 is an above-the-elbow prosthetic assembly. In some embodiments, the combination device 100 is a below-the-elbow prosthetic assembly. In some embodiments, the combination device 100 is an at the wrist prosthetic assembly. In some embodiments, the combination device 100 is an at the finger prosthetic assembly.

Lower Extremity Prosthetic Socket

Figure 4:
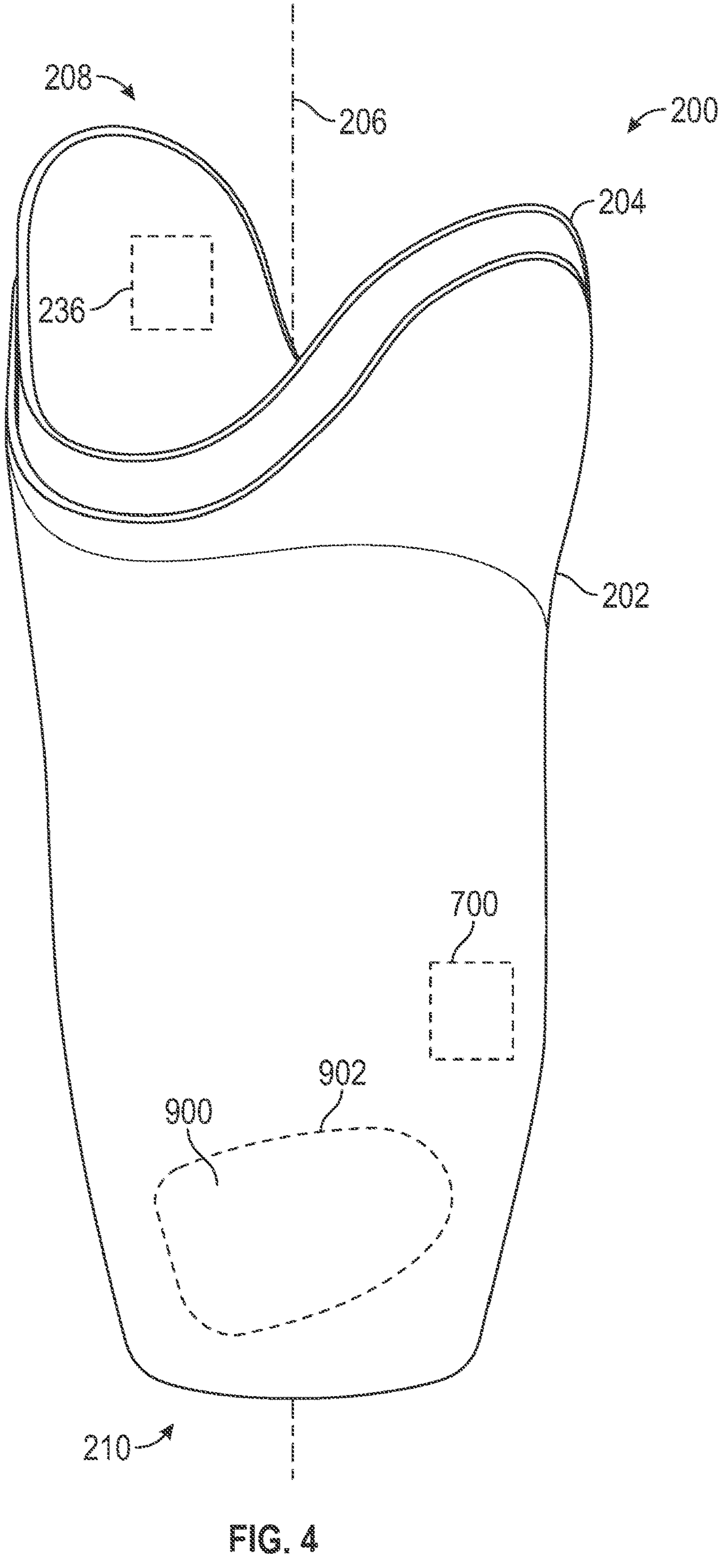
FIG. 4 is a perspective view of a lower limb prosthetic socket and an interfacing liner, according to some embodiments.
Figure 5:
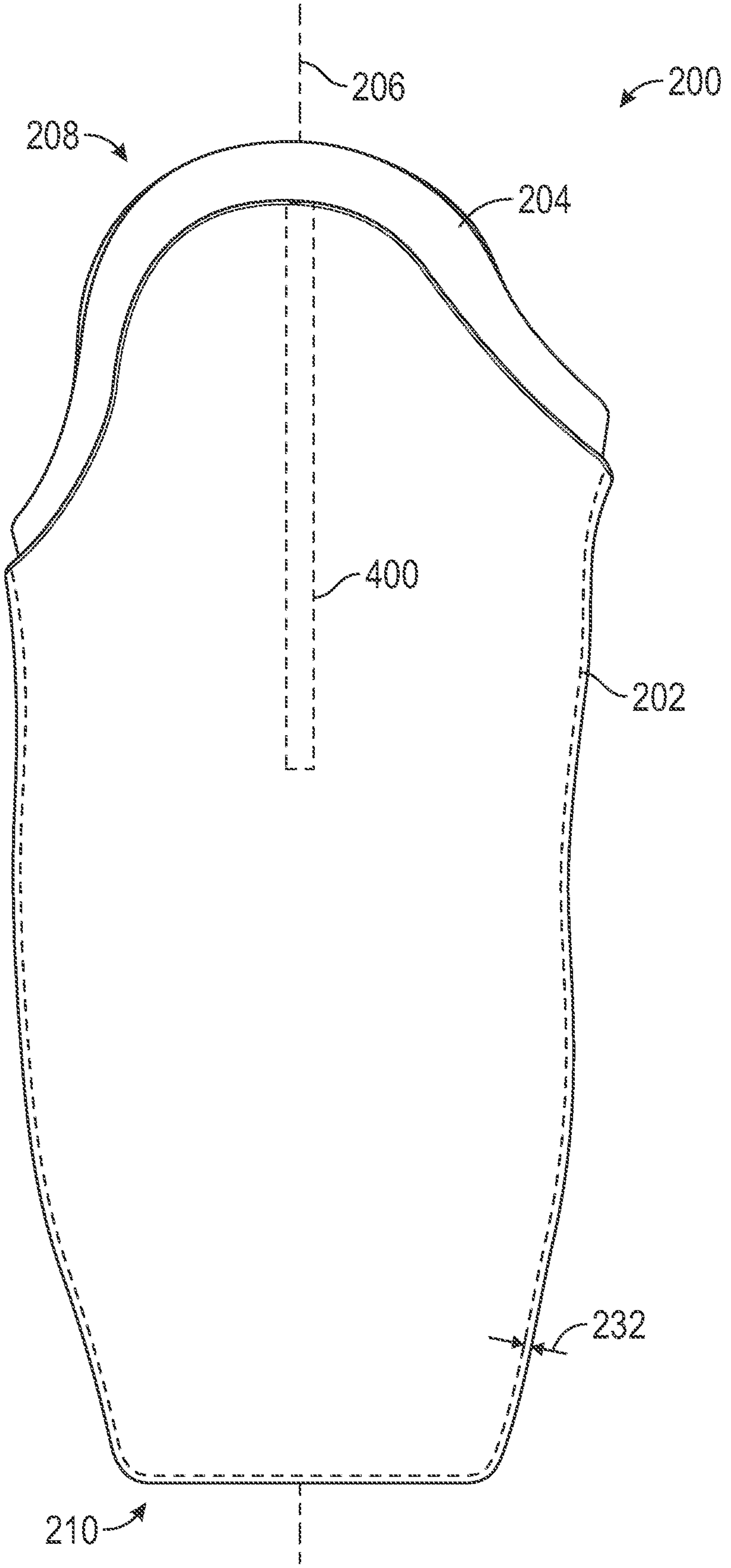
FIG. 5 is a side view of the lower limb prosthetic socket and the interfacing liner of FIG. 4, according to some embodiments.
Figure 6:
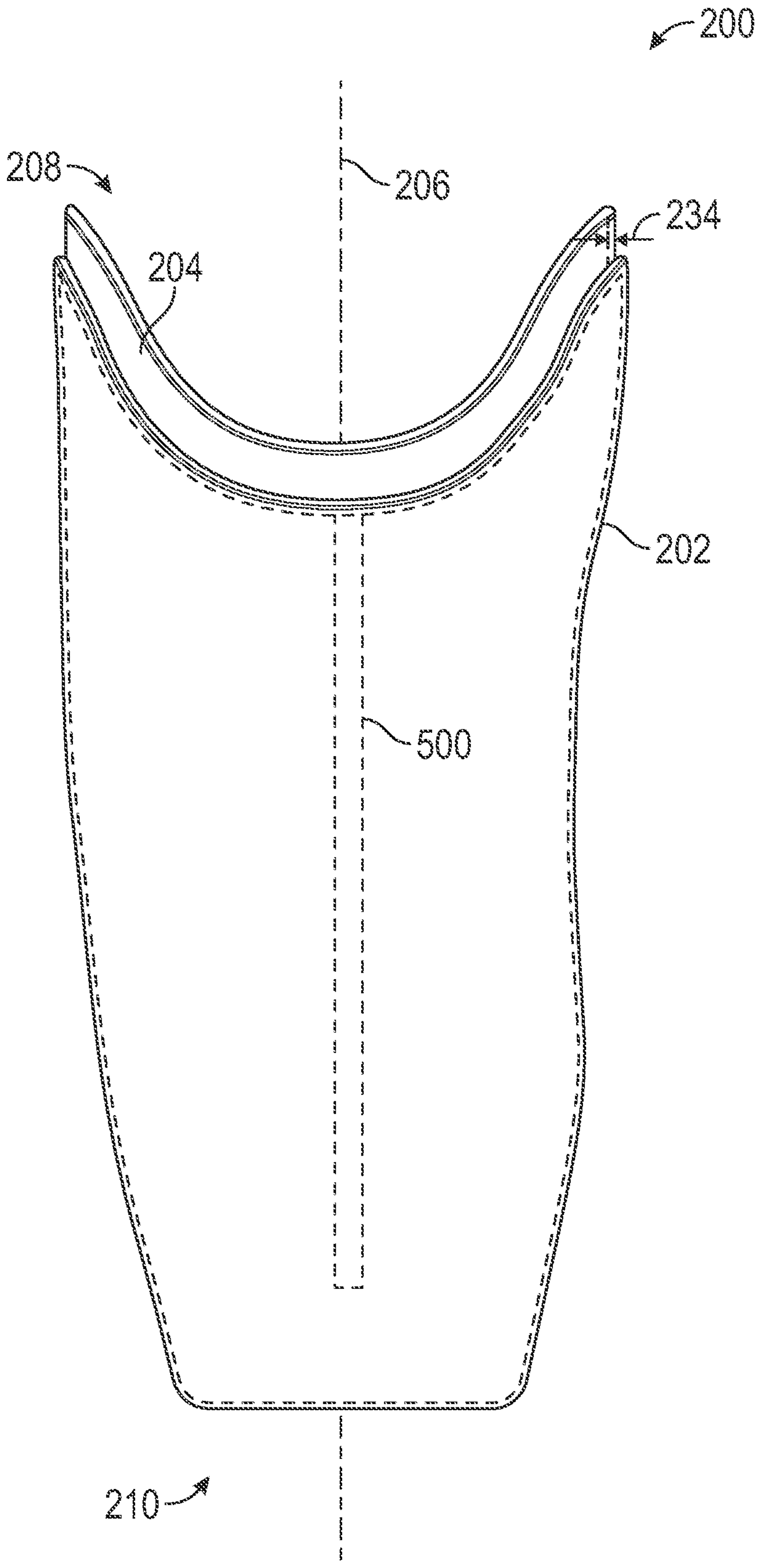
FIG. 6 is a front view of the lower limb prosthetic socket and interfacing liner of FIG. 4, according to some embodiments.

Referring to FIGS. 4-6, a prosthetic assembly, a prosthetic device assembly, a lower prosthetic socket assembly, a combination device, etc., shown as lower extremity combination device 200 includes a socket 202 and a liner 204. The socket 202 and the liner 204 may be similar to the socket 102 and the liner 104 as described in greater detail above with reference to the combination device but are configured for a lower limb application (e.g., an above the knee application, a below the knee application, etc.). The combination device 200 similarly defines a longitudinal axis 206, a first end 208, and a second end 210. In some embodiments, the socket 202 includes interfacing features to couple the combination device 200 with a pylon. It should be understood that the combination device 200 may have any similar features as the combination device 100 but is configured for lower extremity applications. In particular, the combination device 200 may have different geometry or contours specific for the lower limb application. In some embodiments, various internal channels of the combination device 200, as described in greater detail below, are configured to facilitate gravitational force so that moisture travels in a downwards direction. The combination device 200 may also interlock or couple with external componentry similarly to the combination device 100. In some embodiments, the socket 202 and/or the liner 204 include attachment points for the external componentry. In some embodiments, an entirety of the components of the combination device 100 are manufactured through additive manufacturing. In some embodiments, the socket 102 is configured to provide proper distribution of forces across the patient's residual or distal limb.

Interlocking Features

Figure 8:
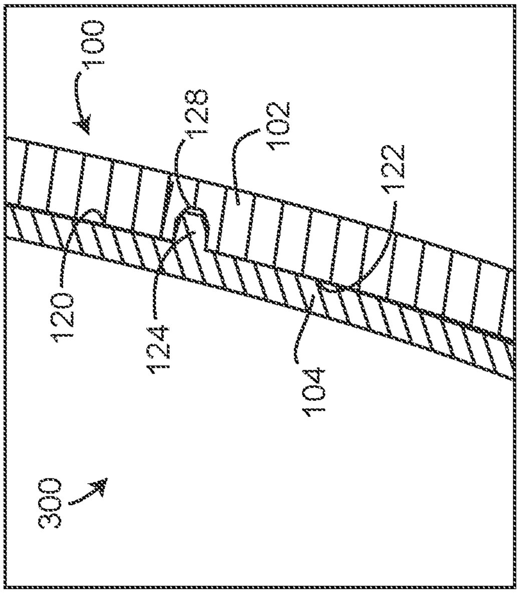
FIG. 8 is a sectional view of interlocking protrusions and recesses of the prosthetic socket and interfacing liner of FIGS. 1-3 or FIGS. 4-6, according to some embodiments.
Figure 7:
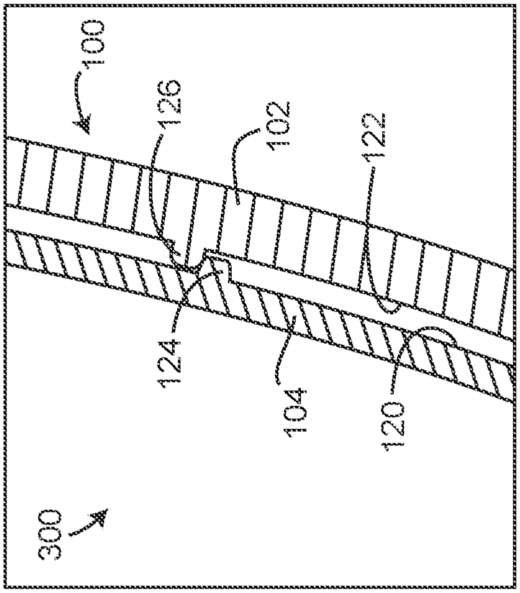
FIG. 7 is a sectional view of interlocking protrusions of the prosthetic socket and interfacing liner of FIGS. 1-3 or FIGS. 4-6, according to some embodiments.

Referring to FIGS. 7-8, the interlocking features 300 are shown according to some embodiments. The interlocking features 300 facilitate removably interlocking or fixing the liner 104 with the socket 102. It should be understood that while the interlocking features 300 are described herein as being disposed on or formed on the socket 102 and the liner 104, the interlocking features 300 shown herein can also be used (e.g., disposed on, formed on, etc.) the socket 202 and the liner 204 of the lower limb combination device 200.

Referring particularly to FIG. 7, an inner surface 122 of the socket 102 includes a protrusion 126 (e.g., an extrusion, an extension, an inwards extending member, etc.). An outer surface 120 of the liner 104 includes a protrusion 124 (e.g., an extrusion, an extension, an outwards extending member, etc.). When the liner 104 is inserted into the socket 102, the protrusion 124 may be translated past the protrusion 126. The protrusions 124 and 126 may abut each other and thereby interlock the liner 104 with the socket 102 (e.g., removably). In some embodiments, one or both of the protrusions 124 and 126 are configured to deform as the liner 104 is inserted into the socket 102 so that sufficient clearance is provided and the protrusions 124 and 126 can be transitioned into the relative arrangement shown in FIG. 7 (or out of the arrangement shown in FIG. 7).

Referring particularly to FIG. 8, the socket 102 includes a recess 128 (e.g., a depression, a groove, a recess, a void, etc.) that is configured to receive the protrusion 124 to removably couple the liner 104 with the socket 102. In some embodiments, the protrusion 124 is configured to deform as the liner 104 is inserted into the socket 102 and expand into the recess 128 to removably couple the liner 104 with the socket 102. In some embodiments, the recess 128 is formed within the outer surface of the liner 104 and the protrusion 124 is formed along the inner surface of the socket 102 so that the protrusion 124 extends from the socket 102 and is received within the recess 128 of the liner 104. It should be understood that the socket 102 and the liner 104, or the socket 202 and the liner 204, may include any number of protrusions, recesses, geometry, etc., or combination thereof, in order to couple the liner 104 with the socket 102 (or to couple the liner 204 with the socket 202) when the liner 104 is inserted into the socket 102 (or when the liner 204 is inserted into the socket 202).

Figure 12:
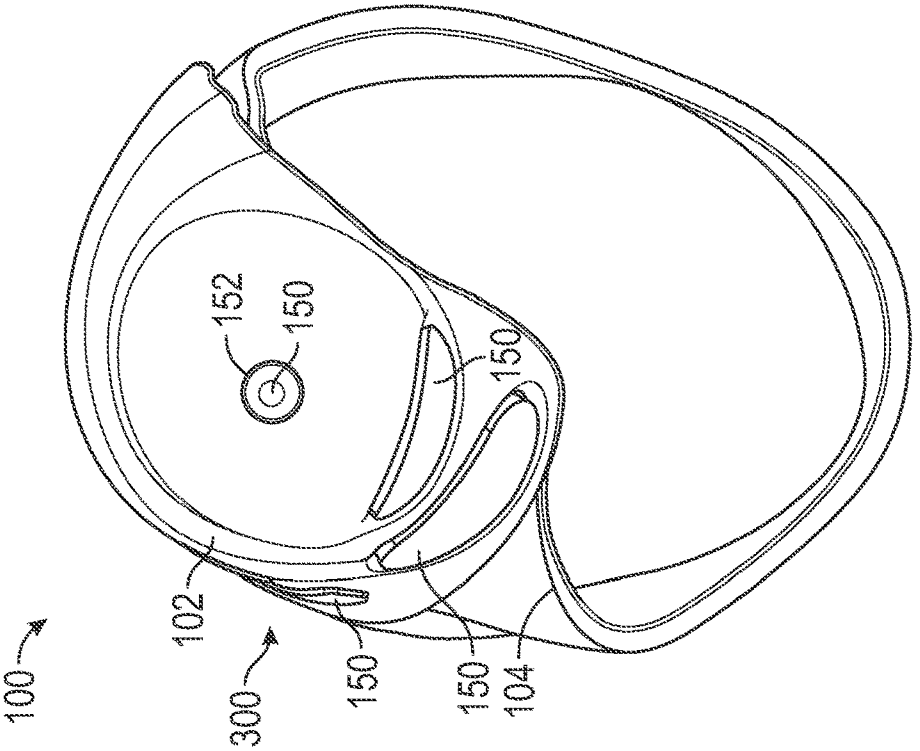
FIG. 12 is a bottom view of the prosthetic socket and interfacing liner of FIG. 10, according to some embodiments.
Figure 11:
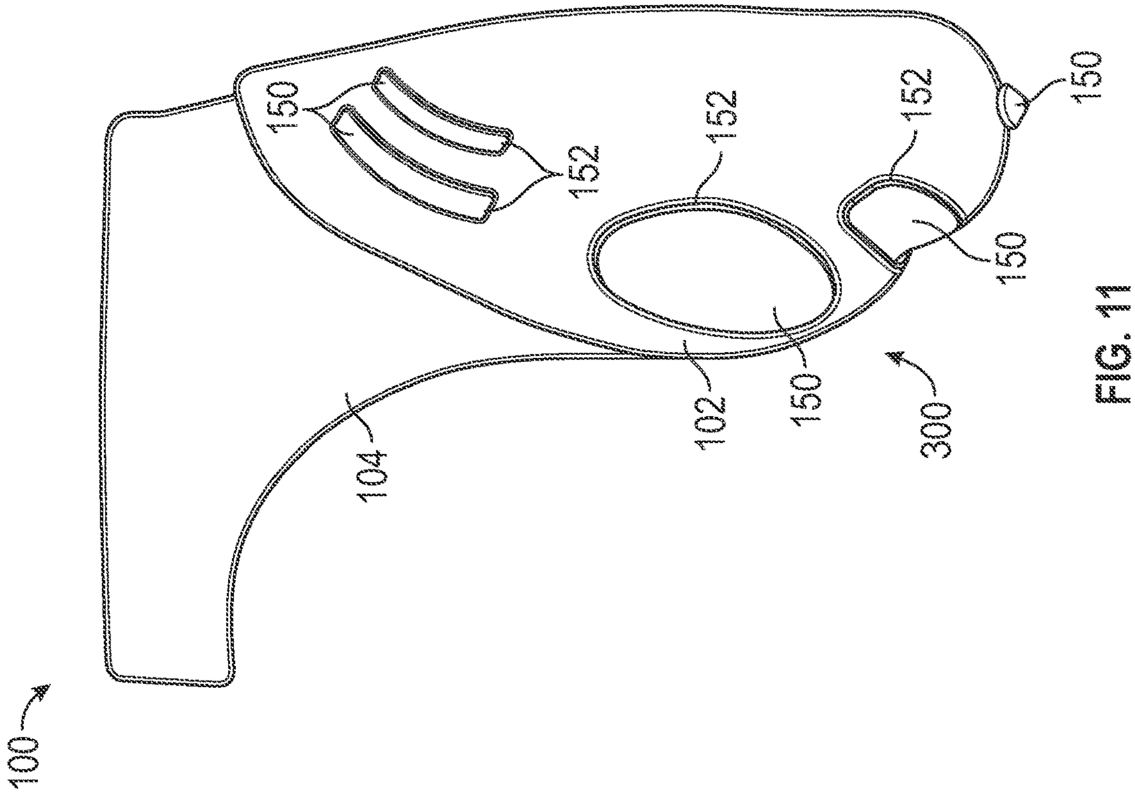
FIG. 11 is a side view of the prosthetic socket and interfacing liner of FIGS. 1-3 or FIGS. 4-6 including interlocking openings and protrusions, according to some embodiments.

Referring to FIGS. 11-12, the interlocking features 300 are shown according to some embodiments. The socket 102 includes multiple openings 152 having shapes corresponding to protrusions 150 of the liner 104. In some embodiments, the protrusions 150 of the liner 104 have irregular shapes, slot shapes, curved shapes, circular shapes, etc., and the socket 102 has openings 152 (e.g., holes, windows, apertures, etc.) having corresponding shapes and positions so that the openings 152 of the socket 102 are configured to receive the protrusions 150 when the liner 104 is inserted into the socket 102 to thereby removably couple (e.g., secure) the liner 104 with the socket 102. In some embodiments, the protrusions 150 of the liner 104 may be used as a gripping surface in addition to an interlocking member to couple the liner 104 with the socket 102. For example, the protrusions 150 can be used to assist the patient in picking up objects using the device 100. The protrusions 150 may provide an interfacing portion having variable geometry (e.g., a "roughened" surface) to improve gripping of the device 100 by a clinician or patient.

Variable Thickness

Referring to FIGS. 2 and 5, the socket 102 or the socket 202 are shown having a thickness 132 or 232, respectively. It should be understood that while the description herein is with reference to the thickness 132 of the socket 102, anything said herein with reference to the thickness 132 of the socket 102 may also be true of the thickness 232 of the socket 202.

In some embodiments, the thickness 132 is uniform along a longitudinal length (e.g., along the longitudinal axis 106). In some embodiments, the thickness 132 is variable or changing along the longitudinal length of the socket 102, and/or along a radial direction as measured about the longitudinal axis 106. In this way, the thickness 132 of the socket 102 can vary (e.g., increase or decrease) along at least one dimension of the socket 102. In some embodiments, the variable thickness 132 defines different zones which have different relative thickness (e.g., thin zones and thicker zones). The thickness 132 may vary in one or two dimensions about the socket 102 in order to accommodate anatomy, requests, and/or needs of the patient.

Referring to FIGS. 3 and 6, the liner 104 and the liner 204 are shown having thickness 134 and thickness 234, respectively. It should be understood that while the description herein is with reference to the thickness 134 of the liner 104, anything said herein with reference to the thickness 134 of the liner 104 may also be true of the thickness 234 of the socket 202.

In some embodiments, the thickness 134 is uniform along the longitudinal length (e.g., along the longitudinal axis 106). In some embodiments, the thickness 134 is variable or changing along the longitudinal length of the liner 104, and/or along a radial direction as measured about the longitudinal axis 106. In this way, the thickness 134 of the socket 102 can vary (e.g., increase or decrease) along at least one dimension of the liner 104. In some embodiments, the varying thickness 134 defines different zones which have different relative thickness (e.g., thin zones and thicker zones). The thickness 134 may vary in one or two dimensions about the liner 104 in order to accommodate anatomy, requests, and/or needs of the patient. The thickness of the liner 104, the liner 204, the socket 102, or the socket 202, may have variable thickness in order to accommodate anatomy, requests, and needs of the patient.

Administered Therapy

Figure 13:
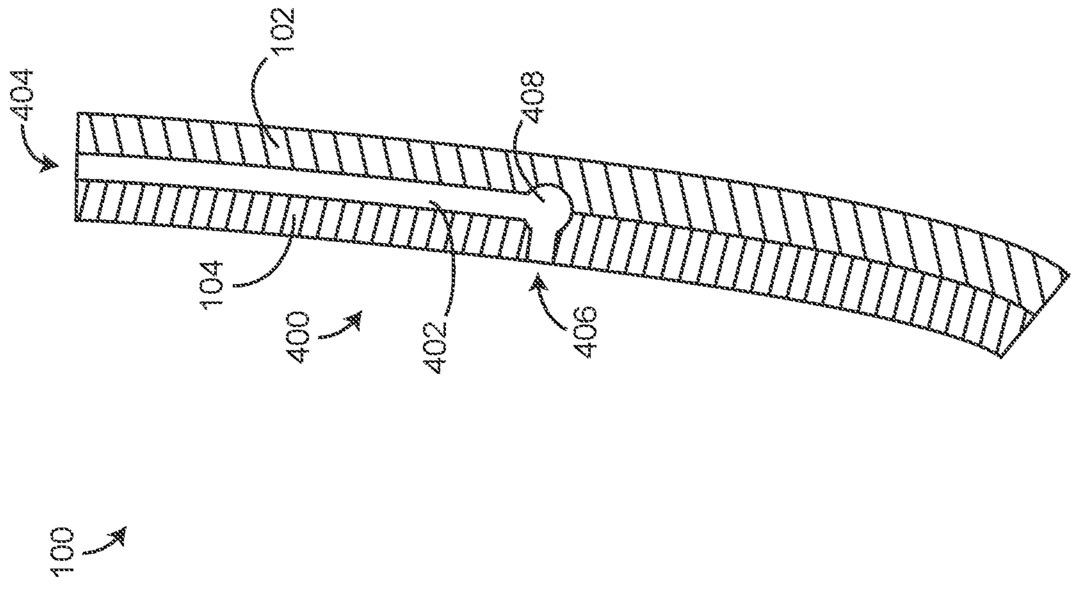
FIG. 13 is a sectional view of the prosthetic socket and interfacing liner of FIGS. 1-3 or FIGS. 4-6 including therapy passageways, according to some embodiments.

Referring to FIGS. 1 and 13, the combination device 100 may include internal passageways, internal voids, passages, openings, channels, pockets, voids, grooves, etc., shown as therapy passages 400. In some embodiments, the therapy passages 400 are formed within the socket 102, within the liner 104, or both the socket 102 and the liner 104 (e.g., between the socket 102 and the liner 104). Referring particularly to FIG. 13, the therapy passages 400 can include a passageway 402, an inlet 404, an outlet 406, and a void 408. In some embodiments, the therapy passages 400 are formed within the socket 102. In some embodiments, the inlet 404 is formed at the first end 108 of the combination device 100 so that therapy or medication can be introduced into the therapy passages 400. In some embodiments, the outlet 406 is configured to deliver the therapy or medication to an interior of the liner 104 so that the medication (e.g., a topical medication) is applied to the patient's distal limb. In some embodiments, the combination device 200 also includes therapy passages 400 as described herein. In some embodiments, the therapy passages 400 are similarly configured as the venting passages 500 or the venting passages 600 described in greater detail below. In some embodiments, the therapy passages 400 can be used to provide anti-inflammatory, anti-bacterial, or pain relief medication to the patient's distal limb. In some embodiments, the therapy passages 400 include multiple perforations or small holes so that the medication is released to the patient's distal limb over time. In some embodiments, the therapy passages 400 are formed entirely within the socket 102 or the socket 202, entirely within the liner 104 or the liner 204, or within both the socket 102 (or the socket 202) and the liner 104 (or the liner 204).

Lattice Structure

Figure 9:
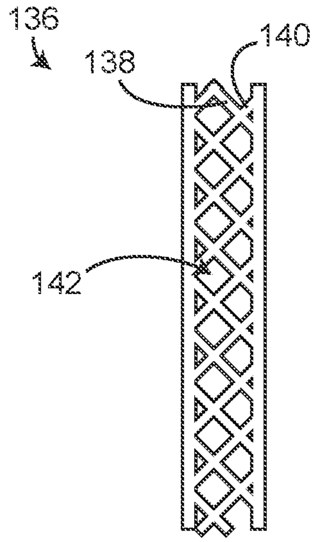
FIG. 9 is a diagram of a lattice structure, according to some embodiments.
Figure 10:
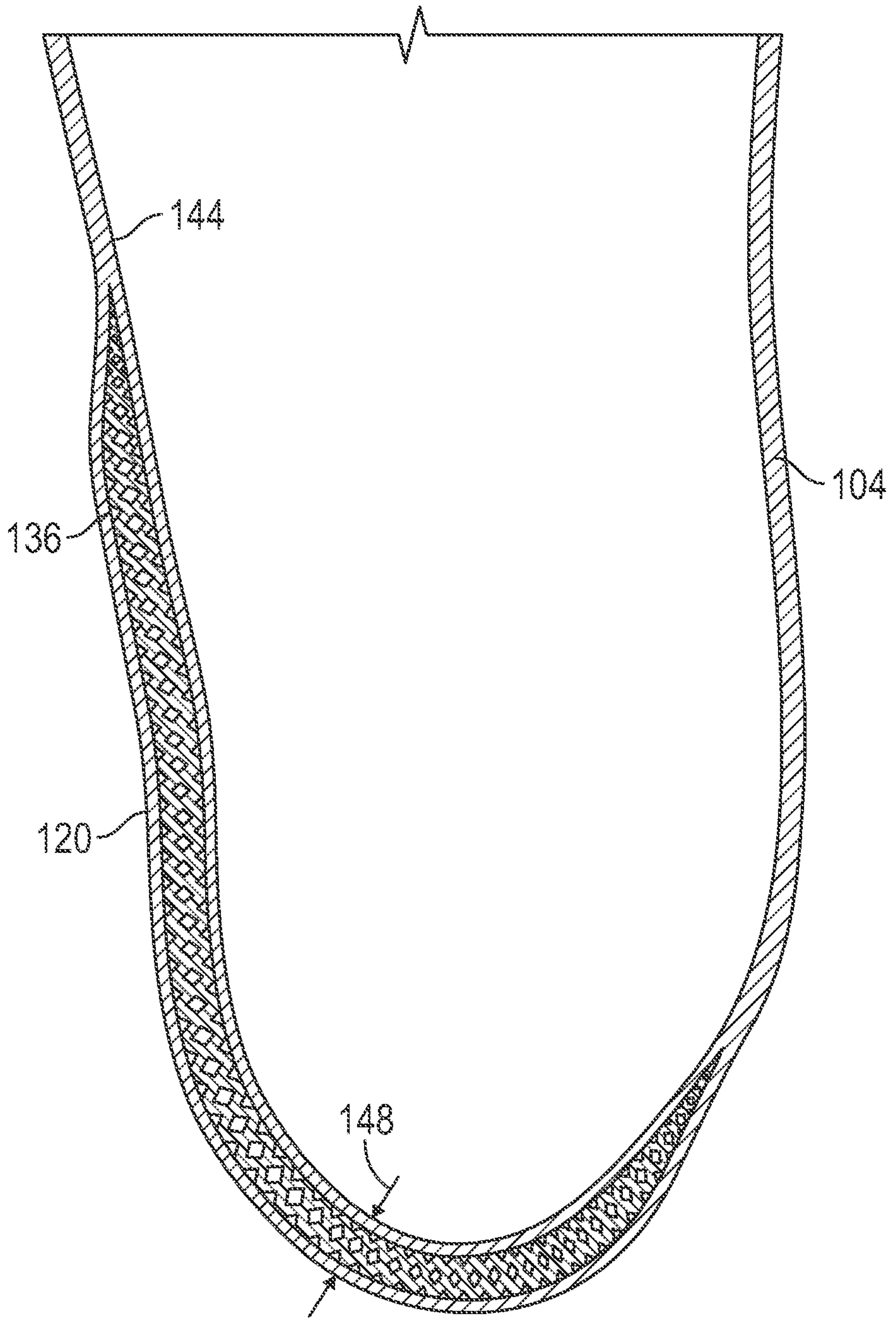
FIG. 10 is a side sectional view of the liner of FIGS. 1-3 or FIGS. 4-6 including the lattice structure of FIG. 9 disposed between walls along a bottom portion of the liner, according to some embodiments.

Referring to FIGS. 3 and 9-10, the liner 104 may include a lattice structure 136 that is configured (e.g., targeted, positioned, etc.) to reduce shear stress and impact forces. In some embodiments, the liner 204 also includes a lattice structure 236 that is the same as or similar to the lattice structure 136 described herein with reference to FIGS. 3 and 9-10. In some embodiments, lattice structures 136 are positioned at a bottom of the liner 104 in order to absorb impact. In some embodiments, the lattice structure 136 are positioned in order to reduce translational forces due to scarring of the patient's limb.

Referring particularly to FIG. 9, the lattice structure 136 is shown to include multiple first members 138 arranged in a first array and extending in a first direction. In some embodiments, the first members 138 extend parallel with each other or are non-parallel with each other. In some embodiments, the first members 138 extend along a substantially straight path. In some embodiments, the first members 138 extend along a curved path. In some embodiments, the first members 138 are spaced uniformly. In some embodiments, the first members 138 are spaced non-uniformly.

Referring still to FIG. 9, the lattice structure 136 further includes multiple second members 140 that are arranged in a second array and extend in a second direction that is different than the first direction. The second members 140 can similarly extend in parallel with each other, or may extend non-parallel with each other. The second members 140 can similarly extend along a substantially straight path, a curved path, may be spaced uniformly and/or may be spaced non-uniformly. The second members 140 and the first members 138 may be integrally formed with each other and can define cells 142 (e.g., open spaces).

Referring particularly to FIG. 10, the lattice structure 136 is disposed along the liner 104 between an interior surface 144 of the liner 104 and the outer surface 120 of the liner 104. In some embodiments, the liner 104 includes double-walled sections (e.g., along a bottom or distal end of the liner 104) within which the lattice structure 136 is positioned. In some embodiments, the lattice structure 136 has a width 146 that can be variable along different portions in order to provide different amount of impact absorption or distribute forces as desired. In some embodiments, the lattice structure 136 is a pattern of depressions or recesses formed in the interior surface 144 of the liner 104 or the outer surface 120 of the liner 104. In some embodiments, the lattice structure 136 is additionally or alternatively disposed on the interior surface 122 of the socket 102. In some embodiments, the lattice structure 136 function as a spring or a damper responsive to forces or compression, and characteristics of the lattice structure 136 (e.g., thickness or width 146 of the double walls, a thickness of the members 138 or 140, etc.) in order to tune a desired dynamic response of the lattice structure 136.

Venting Structures

Figure 14:
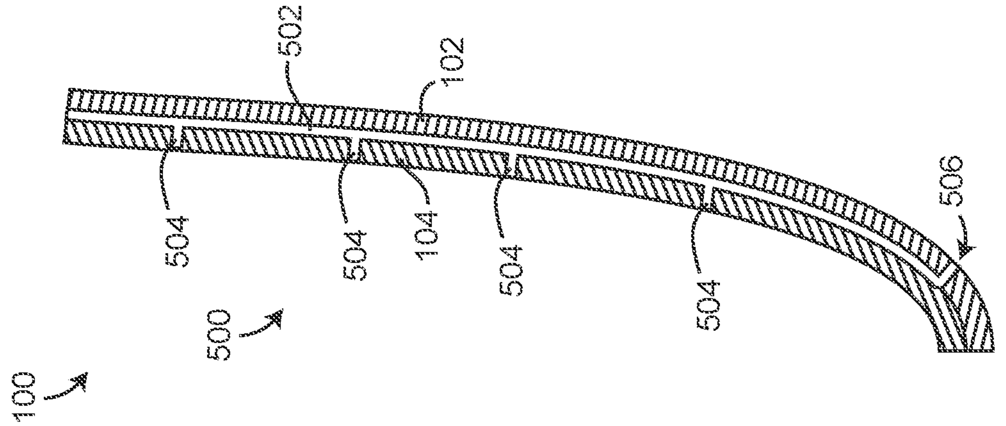
FIG. 14 a sectional view of the prosthetic socket and interfacing liner of FIGS. 1-3 or FIGS. 4-6 including a vent passageway, according to some embodiments.

Referring to FIGS. 1, 6, and 14, the combination device 100 or the combination device 200 may include venting structure 500 that are configured to facilitate improved heat transfer (e.g., heating dispersion) and/or evaporation of bodily fluids of the patient's residual limb. The venting structure 500 can include passageways, passages, etc., configured to fluidly couple different portions of the combination device 100 or the combination device 200 with an external environment to facilitate proper cooling of the patient's residual limb and evaporation of moisture or bodily fluids (e.g., sweat).

Referring particularly to FIG. 14, the venting structure 500 can be formed between the liner 104 and the socket 102 (or between the liner 204 and the socket 202). In some embodiments, the venting structure 500 includes a passageway 502 that extends along a portion of the socket 102. The passageway 502 can be formed within the socket 102, within the liner 104, or cooperatively between the socket 102 and the liner 104 (e.g., with formed recesses between the socket 102 and the liner 104 that cooperatively form the passageway 502 when the liner 104 is installed into the socket 102). In some embodiments, the venting structure 500 includes one or more openings, holes, bores, apertures, perforations, slots, etc., shown as passages 504 that extend through the liner 104 so that an interior of the liner 104 (e.g., within which the patient's residual limb is positioned) can fluidly couple with the passageway 502. In some embodiments, the venting structure 500 also includes an outlet 506 (e.g., an opening, a hole, a bore, a passage, etc.) formed in the socket 102 that vents the passageway 502 to an external environment of the socket 102. In some embodiments, the outlet 506 is formed and extends through the socket 102 (e.g., a sidewall of the socket 102). In some embodiments, the combination device 100 includes multiple venting structures 500 disposed about the combination device 100 (or the combination device 200) that facilitate improved heat transfer (e.g., cooling) and evaporation (e.g., of sweat) to facilitate improved comfort for the patient when wearing the combination device 100 or the combination device 200.

Figure 15:
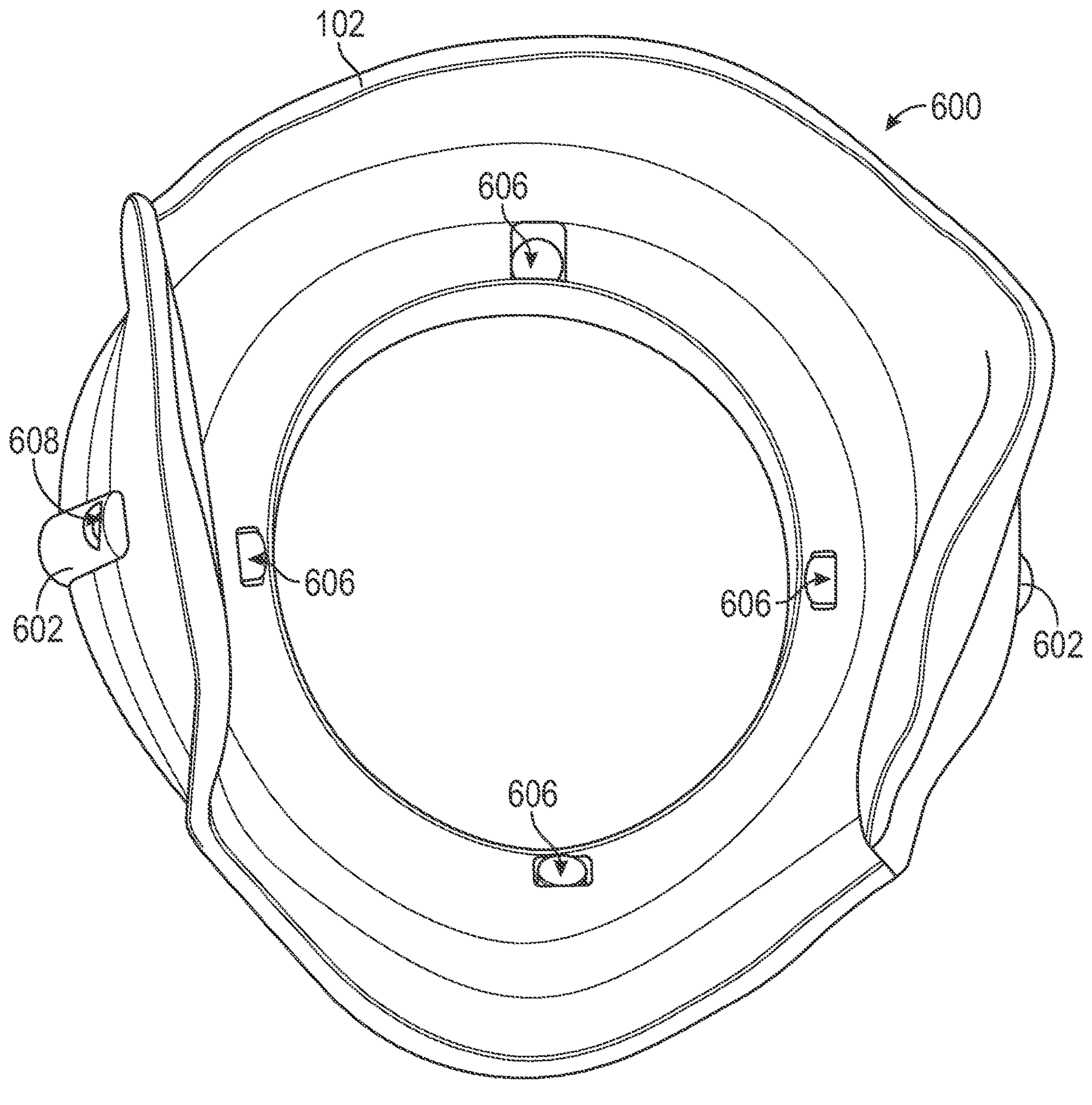
FIG. 15 is a top view of the socket of FIGS. 1-3 illustrating venting channels and openings, according to some embodiments.
Figure 16:
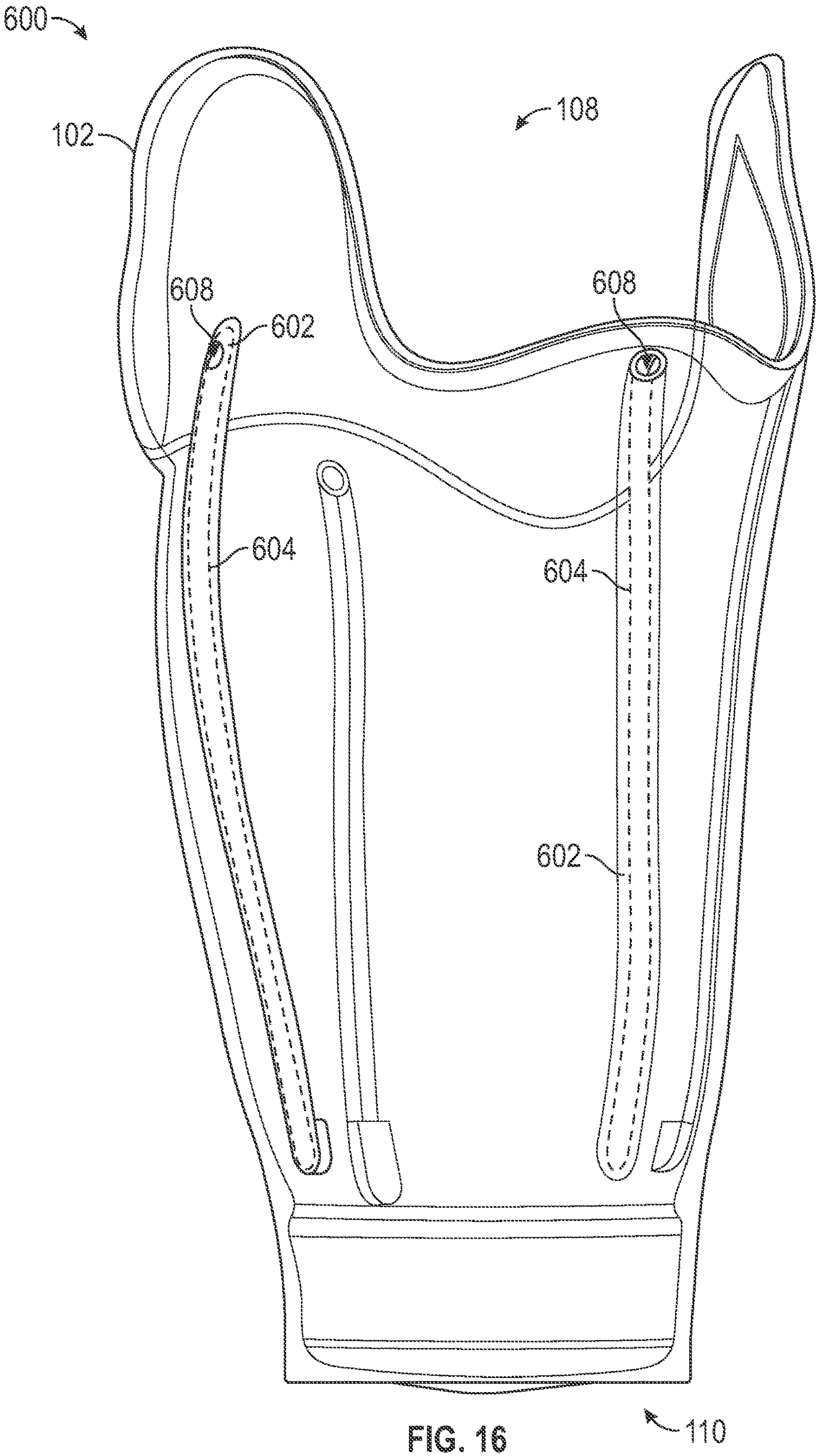
FIG. 16 is a side view of the socket of FIG. 15 illustrating the venting channels, according to some embodiments.

Referring to FIGS. 15-16, the venting structure 500, shown as venting structures 600, may be formed within the socket 102. The socket 102 is shown to include multiple vents (e.g., channels) formed within walls of the socket 102. The socket 102 may include ribs, ridges, etc., shown as protrusions 602 that extend lengthwise along the socket 102. The venting structure 600 includes channels 604 (e.g., passages, inner volumes, voids, etc.) that extend through the protrusions 602 in the lengthwise direction. The venting structures 600 also include openings 608 positioned at a first end of the channels 604 (e.g., at an upper end of the channels 604, proximate the first end 108) disposed on an outer surface of the socket 102, and openings 606 positioned at a second end of the channels 604 (e.g., at a lower end of the channels 604, proximate the second end 110) disposed on the inner surface 122 of the socket 102. The venting structure 600 can be used alternatively or in addition to the venting structure 500. In some embodiments, the openings 606 are configured to correspond or match with correspondingly positioned openings, channels, inner volumes, recesses, etc., of the liner 104 when the liner 104 is installed in the socket 102. The venting structures 600 are configured to facilitate improved cooling, airflow, and evaporation. The venting structure 600 can also be used to provide therapy to the patient's distal limb or to receive electrical components. It should be understood that any number of venting structures 600 may be used in the combination device 100 or the combination device 200.

In some embodiments, one or more of the channels, vents, internal volumes, etc., described herein with reference to FIGS. 13-16 can be used to dissipate heat, with separate channels to dissipate moisture. Channels that are used to dissipate moisture may direct the moisture downwards (e.g., in a direction of gravitational force) so that the moisture is drawn out of the combination device 100 or the combination device 200. Channels that are used to dissipate heat may generally extend outwards. In some embodiments, the combination device 100 or the combination device 200 include openings that extend through their liners and sockets and are aligned when assembled so that heat may be dissipated outwards.

Electrical Components

Figure 17:
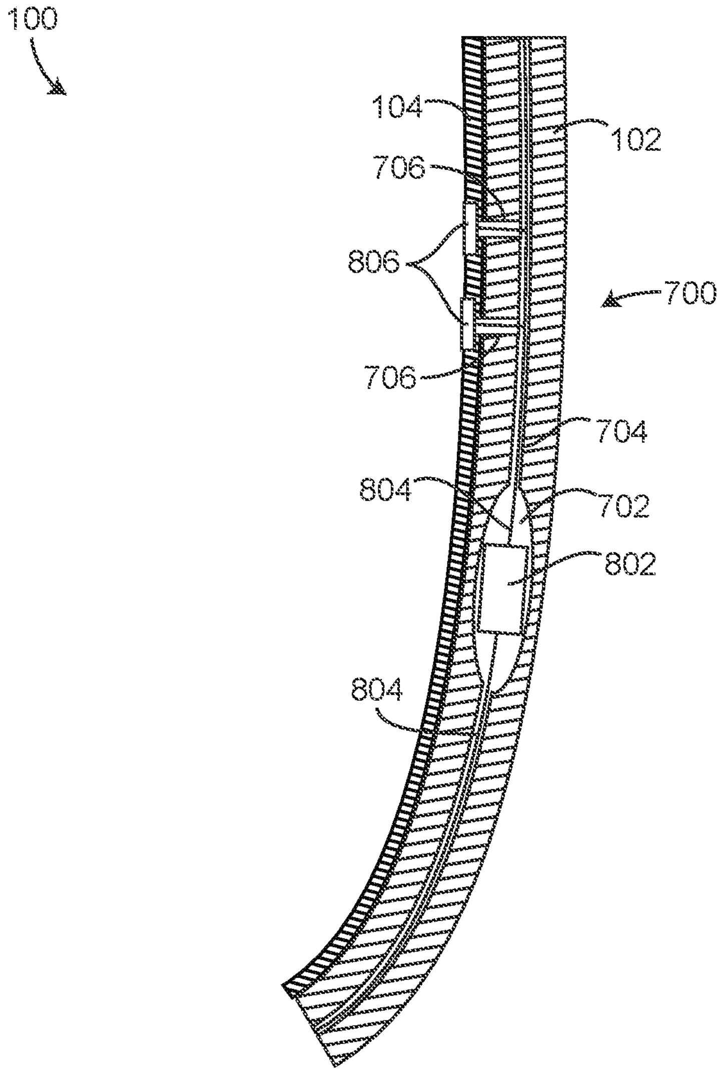
FIG. 17 is a side sectional view of the socket of FIGS. 1-3 or the socket of FIGS. 4-6 including electrical channels and/or voids configured to receive one or more electrical components, according to some embodiments.

Referring to FIGS. 1, 4, and 17, the combination device 100 and/or the combination device 200 include one or more electrical voids 700 configured to receive one or more electrical components such as sensors, wires, controllers, batteries, circuits, feedback devices, etc. In some embodiments, the electrical voids 700 are formed in the socket 102 and are configured to enclose or substantially surround the electrical components. In some embodiments, the electrical voids 700 are configured to receive a Peltier cooling system and components of the Peltier cooling system. In some embodiments, the electrical voids 700 are configured to receive myoelectric parts, a stimulus unit (e.g., a TENS unit), etc.

As shown in FIG. 17, the socket 102 (or alternatively the socket 202) may include a channel 704 (e.g., a passageway, a passage, an elongated void, etc.) that extends along a length of the socket 102. In some embodiments, the electrical voids 700 (e.g., channels, inner volumes, bores, apertures, internal structure, etc.) includes a chamber 702 within the socket 102 that is configured to receive an electrical device 802 (e.g., a controller, a microcontroller, a microprocessor, a programmable logic controller, a battery, a battery cell, an energy storage device, etc.). In some embodiments, the channel 704 is configured to receive one or more electrical cords, shown as cords 804. The cords 804 can extend through the inner volumes of the socket 102 and provide electrical power to various of the electrical devices of the combination device 100 and/or to provide electrical communications to or from the various electrical devices. In some embodiments, the electrical voids 700 include one or more passageways 706 that extend through the socket 102 towards the liner 104. The liner 104 can also include one or more portions of the passageways 706 through which the cords 804 extend. In some embodiments, one or more sensors or feedback devices, shown as electrical input/output devices 806 are electrically coupled with the cords 804. In some embodiments, the cords 804 are myoelectric wires. In some embodiments, the electrical device 802 and the electrical input/output devices 806 are configured to communicate wirelessly (or wirelessly with an external computing device such as a smart phone) using a wireless communications protocol such as Bluetooth, LoRa, Zigbee, Near Field Communications, etc.

The electrical input/output devices 806 may be received within a recess or a groove on an inner surface of the liner 104. In some embodiments, the electrical input/output device 806 include any of, or any combination of, a temperature sensor, a cooling device, a humidity sensor, a tactile feedback device, a haptics feedback device, an electrical stimulation feedback device, a force transducer, a biomechanical interface, a microprocessor knee, electrodes, etc. The electrical input/output devices 806 may generally be transducers that are configured to use electrical energy and/or communications to provide feedback to the patient's residual limb, or that are configured to monitor a condition and generate communications responsive to and related to the condition (e.g., temperature, humidity, etc.).

Selective Vacuum Regions

Referring to FIGS. 3 and 4, the combination device 100 or the combination device 200 can include vacuum sections or regions, shown as vacuum regions 900. The regions 900 may be fluidly sealed and decoupled from other regions between the socket 102 and the liner 104 (or between the socket 202 and the liner 204). In some embodiments, the vacuum regions 900 include a seal 902 that extends along a path defining boundaries of the vacuum regions 900. The seal 902 may be formed on the outer surface 120 of the liner 104 or the liner 204, and the inner surface 122 of the socket 102 or the socket 202. In some embodiments, the seal 902 has the form of a protrusion on outer surface 120 of the liner 104 or the liner 204 that extends to define the boundary of the vacuum region 900. The protrusion (e.g., the seal 902) may seal with the corresponding inner surface 122 of the socket 102 or the socket 202. The seal 902 may also have the form of a protrusion on the inner surface 122 of the socket 102, or a channel on the inner surface 122 of the socket 102 that receives the protrusion on the outer surface 120 of the liner 104 to thereby fluidly seal the liner 104 with the socket 102. In some embodiments, an inner volume is defined between the outer surface 120 of the liner 104 and the inner surface 122 of the socket 102, with a perimeter or boundary defined by the seal 902. Advantageously, the vacuum regions 900 can be designed or disposed around the combination device 100 or the combination device 200 in order to provide desired therapy for the patient. In some embodiments, the socket 102 and the liner 104 (or the socket 202 and the liner 204) can be design such that indexing between the socket 102 and the liner 104 facilitate certain sections of the combination device 100 (or the combination device 200) to function under vacuum while other sections do not function under a vacuum for proper device suspension.

Additive Manufacturing Process

Figure 18:
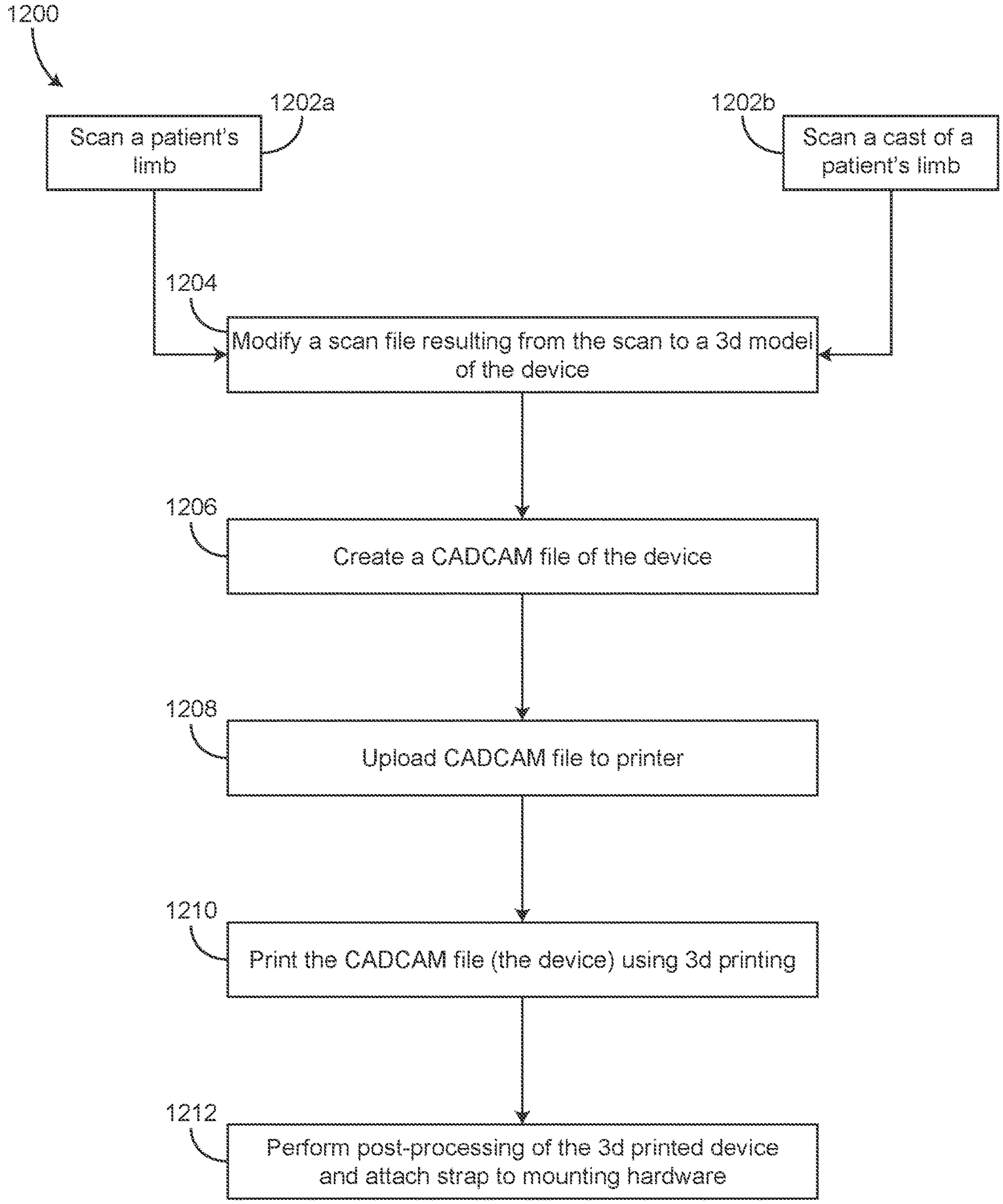
FIG. 18 is a flow diagram of a process for additively manufacturing any of the prosthetic devices of FIGS. 1-17, according to some embodiments.

Referring particularly to FIG. 18, a flow diagram of a process 1200 for producing or manufacturing the combination device 100 or the combination device 200 is shown, according to some embodiments. Process 1200 includes steps 1202-1212 and can be performed using an additive manufacturing system (e.g., system 1300 as described in greater detail below with reference to FIG. 19).

Process 1200 includes scanning a patient's distal or residual limb (step 1202*a*) or scanning a cast of a patient's distal limb (step 1202*b*). In some embodiments, step 1202*a* or step 1202*b* is performed using a scanning device (e.g., scan device 1312 as described in greater detail below with reference to FIG. 19). The patient's limb can be scanned directly (step 1202*a*), or a cast of the patient's limb may be scanned (step 1202*b*). In some embodiments, performing step 1202*a* or step 1202*b* results in the generation of a scan file.

Process 1200 includes modifying a scan file resulting from the scan (e.g., resulting from performing step 1202*a* or step 1202*b*) to a 3d model of a device (e.g., the liner 104, the socket 102, the liner 204, and/or the socket 202) (step 1204), according to some embodiments. In some embodiments, step 1204 is performed on a computer system based on one or more user inputs or inputs from a health care provider. For example, step 1204 can include adjusting a thickness of the device of the scan file at different locations. In some embodiments, step 1204 includes digitally using buildups or reductions to the thickness of the 3d model of the device to achieve a desired thickness that yields a desired corresponding deformation or flexion when the device is loaded. Step 1204 may include performing smoothing on the 3d model. For example, step 1204 can be performed by computer system 1302 based on one or more user inputs or inputs from a health care provider obtained from user device 1310 (described in greater detail below with reference to FIG. 19). In some embodiments, step 1204 includes defining channels, voids, passages, inner volumes, etc., in order to provide venting passages, therapy passages, heat dissipation passages, electrical device voids, etc. In some embodiments, step 1204 includes adding geometry to the 3d model of the devices (e.g., the liner 104 and the socket 102) so that the liner 104 and the socket 102 are configured to interlock when assembled. In some embodiments, step 1204 includes positioning or adding lattice structures along various portions of the liner of the 3d models of the device (e.g., the liner 104, the liner 204, etc.). The step 1204 can include defining (e.g., on the 3d models) any of the geometry of the venting passages 600, the venting passages 500, the electrical voids 700, the therapy passages 400, the protrusions 150, the openings 152, the lattice structures 136, the protrusions 124, the protrusions 126, or the recesses 128.

Process 1200 includes creating a computer assisted design (CAD) and/or a computer assisted manufacturing (CAM) file of the device (e.g., the liner 104 and the socket 102, the liner 204 and the socket 202, etc.) (step 1206), according to some embodiments. Process 1200 also includes uploading the CAD/CAM file to a printer (e.g., 3d printer 1314) (step 1208), according to some embodiments. Steps 1206 and 1208 can be performed by computer system 1302 (e.g., in response to a user input such as from a health care provider) as described in greater detail below with reference to FIG. 19.

Process 1200 includes printing the CAD/CAM file using 3d printing (e.g., to generate the device, the combination device 100, the combination device 200, etc.) (step 1210), according to some embodiments. In some embodiments, step 1210 includes performing additive manufacturing (e.g., dispensing or outputting layers consecutively on top of each other) to produce the device. In some embodiments, the additive manufacturing is performed using a single uniform material such as a thermoplastic (e.g., nylon, a flexible silicone or similar material, etc.) or a thermoplastic reinforced with high strength material (e.g., a thermoplastic infused with carbon). The resulting device or 3d printed component can have variable thickness as defined by the CAD/CAM file. In some embodiments, both of the liner 104 and the socket 102 (or the liner 204 and the socket 202) are manufactured from a single uniform material such as silicone. In some embodiments, the liner 104 is an integrally formed piece, and the socket 102 is similarly a single, integrally formed piece. The liner 204 may also be a single integrally formed piece, and the socket 202 may also be a single, integrally formed (e.g., continuous) piece. In some embodiments, using flexible silicone, and/or the presence of voids, internal passages, etc., facilitates reduced weight of the combination device 100 or the combination device 200. Advantageously, reducing the weight of the combination device 100 or the combination device 200 may facilitate improved patient comfort.

Process 1200 includes performing post-processing on the 3d printed device (step 1212), according to some embodiments. For example, step 1212 can include removing excess material that is dispensed during step 1210 (e.g., during fabrication of the device). Step 1212 can be performed by a technician. Additional post-processing can be performed based on anatomy or needs of the patient. In some embodiments, the socket 102 and the liner 104, or the socket 202 and the liner 204 can be modified or adjusted (e.g., by applying heat and being deformed) to provide proper distribution of forces across the patient's distal limb after the fabrication process. In some embodiments, the socket 102, the liner 104, the socket 202, and/or the liner 204 are configured to be adjusted a minor amount after being manufactured without sustaining structural damage.

In some embodiments, the device that is produced by performing process 1200 is a lower extremity prosthetic socket, with a varying thickness (e.g., cross-sectional thickness) throughout. The device can provide proper stability and distribution of forces when worn, and is produced using additive manufacturing techniques. The thickness of the device can be modified in any area to accommodate the anatomy of the patient as well as any additional requirements the patient may have. The device is created using 3D printing, wherein the material composition is of a single uniform substance and can provide extra comfort to the patient when worn due to its lightweight properties, according to some embodiments.

Additive Manufacturing System Architecture

Figure 19:
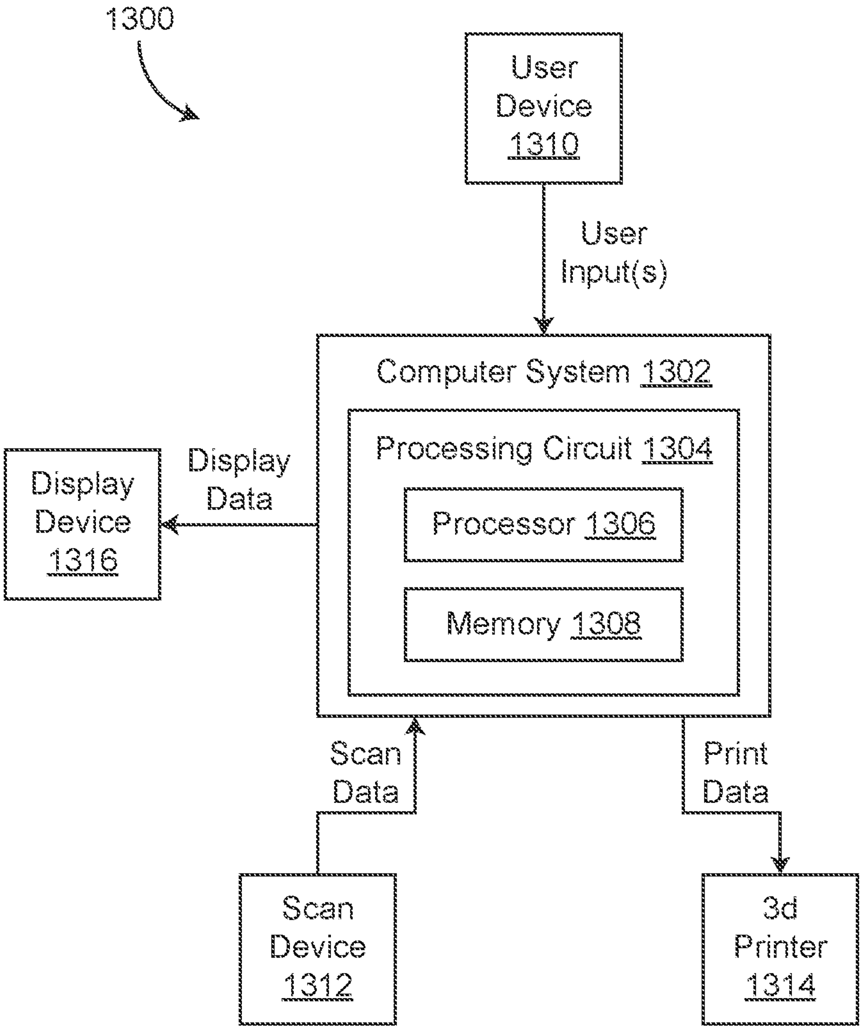
FIG. 19 is a block diagram of an additive manufacturing system architecture configured to implement the process of FIG. 18, according to some embodiments.

Referring now to FIG. 19, a system 1300 for additive manufacturing of prosthetic, orthotic, or protective devices is shown, according to some embodiments. System 1300 includes a user device 1310, a display device 1316, a computer system 1302, a scan device 1312, and a 3d printer or additive manufacturing machine 1314.

Computer system 1302 is configured to receive scan data from scan device 1312, according to some embodiments. Computer system 1302 can be a desktop computer, a laptop, a remote computing system, a smart phone, a tablet, a personal computing device, etc. Computer system 1302 includes a processing circuit 1304 having memory 1308 and a processor 1306. Processor 1306 can be implemented as a general-purpose processor, an application specific integrated circuit (ASIC), one or more field programmable gate arrays (FPGAs), a group of processing components, or other suitable electronic processing components.

Memory 1308 (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present application. Memory 1308 may be or include volatile memory or non-volatile memory. Memory 1308 may include database components, object code components, script components, or any other type of information structure for supporting the various activities and information structures described in the present application. According to an exemplary embodiment, memory 1308 is communicably connected to processor 1306 via processing circuit 1304 and includes computer code for executing (e.g., by processing circuit 1304 and/or processor 1306) one or more processes described herein.

Computer system 1302 can be configured to run CAD computer software to facilitate the design and production of any of combination device 100 and/or combination device 200, or the components of combination device 100 or combination device 200 thereof. Computer system 1302 is configured to receive scan data from scan device 1312, according to some embodiments. In some embodiments, the scan data is a scan file obtained from scan device 1312. In some embodiments, a technician may scan device 1312 to scan a patient's residual limb or a cast of the patient's residual limb, thereby generating the scan data.

When the scan data is provided to computer system 1302, computer system 1302 can generate a CAD or CAM file. A user (e.g., a health care provider) can then provide inputs (e.g., via user device 1310) to adjust geometry, thickness, etc., of the CAD or CAM file. More generally, computer system 1302 may use the scan data to generate a digital representation of a device to be manufactured for the patient's residual limb. Computer system 1302 can provide display data to display device 1316 (e.g., a computer screen, a display screen, etc.) so that the digital representation is visually displayed in real-time. The user or health care provider can then view real-time changes or updates as the user changes or adjusts the CAD or CAM file.

For example, the user may adjust the CAD or the CAM file so that the design gradually tapers or thickens in different areas. In some embodiments, the user or the health care provider may use data from different experiments to identify areas where a patient may experience high stress. The user may decrease thickness of the CAD or CAM file at areas where high stress is experienced so that the 3d printed device may flex or deform. This can allow the 3d printed device to be more comfortable for the patient. In some embodiments, thickness of the 3d printed devices is maintained above a minimum thickness value. The user can also use knowledge regarding different weight lines of the patient to determine which areas of the CAD or CAM file/model should have decreased or increased thickness. The user may also use historical data to determine which areas or portions of the 3d printed device or the CAD/CAM file/model should have increased or decreased thickness (e.g., wall thickness). The user may also use the CAD/CAM file or model in order to produce a model of a mold.

Once the user (e.g., the health care provider) has adjusted or manipulated the CAD/CAM file/model, the user can prompt computer system 1302 to export the file/model to 3d printer 1314 as print data. Computer system 1302 can convert the adjusted, manipulated, or updated CAD/CAM file/model to a file type that is compatible with 3d printer 1314 (e.g., a Standard Tessellation Language (STL) file). Computer system 1302 then provides the print data to 3d printer 1314.

The 3d printer 1314 can be any additive manufacturing machine or device that is configured to successively provide or discharge layers of material onto each other to form or construct a part. 3d printer 1314 may be configured to dispense material (e.g., one or more powder materials that can form nylon when combined with fusing/detailing agents and exposed to fusing light, or any other dispensable materials) in layers to fabricate the CAD/CAM file. The 3d printer 1314 may manufacture parts directly or may manufacture molds of parts for use in an injection molding process.

Advantageously, the systems and methods described herein can be used to produce 3d printed prosthetics, orthotics, or protective devices that interlock with each other, and include various internal passages for medication, therapy, electrical component placement, heat transfer, or evaporation (e.g., venting). Traditional molding methods do not offer the same flexibility of variable wall thickness, the ability to provide integrally formed interlocking members, and various internal passages, voids, or buildups.

Injection Molding Process

Figure 20:
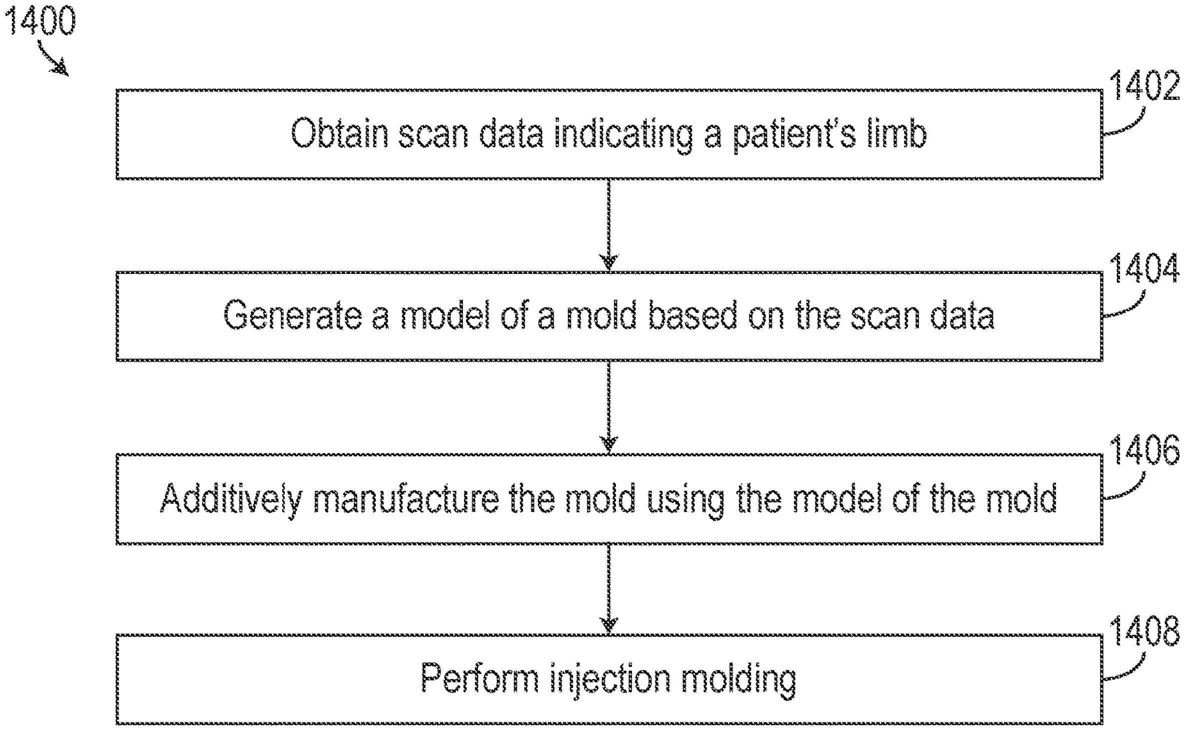
FIG. 20 is a flow diagram of a process for manufacturing any of the prosthetic devices of FIGS. 1-17 using injection molding, according to some embodiments.

Referring particularly to FIG. 20, a flow diagram of a process 1400 for producing or manufacturing the combination device 100 or the combination device 200 is shown, according to some embodiments. Process 1400 includes steps 1402-1408 and can be performed using an additive manufacturing system (e.g., system 1300). Process 1400 may be performed to advantageously facilitate injection molding of one or more custom fit components for a patient. For example, the process 1400 can advantageously combine scanning techniques with additive manufacturing techniques and injection molding techniques to provide a robust custom-fit prosthetic or orthotic. The process 1400 can be performed using a flexible silicone material, a higher durometer rubber, or any other material capable of being injection molded. The process 1400 can be performed to additively manufacture a mold and to perform injection molding using a silicone material having a shore between 20a and 70a.

Process 1400 includes obtaining scan data indicating a patient's limb (step 1402), according to some embodiments. The patient's limb can be a patient's residual limb or a patient's distal limb. Step 1402 can include performing step 1202*a* or step 1202*b* of process 1200, as described in greater detail above. For example, step 1402 may include obtaining scan data of a patient's residual limb, a cast of the patient's limb, etc., using a scanning device. The scan data may indicate geometry of the patient's residual limb and can be used as a basis for designing a prosthetic or orthotic for the patient.

Process 1400 includes generating a model of a mold based on the scan data (step 1404). The model of the mold may be a model of any of the liner 104, the socket 102, the liner 204, or the socket 202. The model may be a CAD model, a CAM model, or any other computer design model indicating geometric shape and size of the liner 104, the socket 102, or the socket 202. In some embodiments, step 1404 can include performing step 1204 of process 1200, as described in greater detail above. Step 1404 may include performing one or more modeling techniques (e.g., buildups, extrusions, reductions, adjustments, etc.) in order to produce the model based on the scan data. The model of the mold can have the form of a cavity configured to receive an injection of a material in order to produce any of the liner 104, the socket 102, or the socket 202. It should be understood that step 1404 can include the development and generation of a single model of a mold, or multiple models of molds that are configured to interlock and couple with each other (e.g., the socket 102 and the liner 104). Step 1404 can also include defining various channels or inner volumes that may be contained within a single device or defined between a first and a second device when assembled. For example, step 1404 can include defining channels, voids, passages, inner volumes, etc., in the model of the mold in order to provide venting passages, therapy passages, heat dissipation passages, electrical device voids, etc.

Process 1400 includes additively manufacturing the mold using the model of the mold generated in step 1404 (step 1406), according to some embodiments. In some embodiments, step 1406 can include performing any of steps 1206, 1208, or 1210 of process 1200, as described in greater detail above with reference to FIG. 18. For example, step 1406 can include creating a CAD/CAM file of the mold (step 1206), uploading the CAD/CAM file of the mold to a printer (e.g., 3d printer 1314) (step 1208), and printing the CAD/CAM file using 3d printing (step 1210) to additively manufacture the mold. In some embodiments, step 1406 includes converting the model of the mold into a format that is usable by an additive manufacturing system. Step 1406 may include generating instructions for a layer by layer additive manufacturing process (e.g., printhead paths and deposit controls) in order to additively manufacture the mold.

Process 1400 includes performing injection molding on the mold (step 1408), according to some embodiments. Step 1408 may be performed by injecting a material into the mold additively manufactured in step 1306 to construct the device (e.g., device 100, device 200, etc.). In some embodiments, the material that is injection molded into the mold to manufacture the device can be a single uniform material such as a thermoplastic (e.g., nylon, a flexible silicon or similar material, etc.). The material may additionally or alternatively be a higher durometer rubber such as thermoplastic polyurethane. In some embodiments, process 1400 can include post-processing of the device, as described in greater detail above with reference to step 1212 of FIG. 18. Advantageously, process 1400 combines scanning processes, modeling processes, additive manufacturing, and injection molding in order to provide a robust custom-fit prosthetic or orthotic. It should be understood that process 1400 as described herein with reference to FIG. 20 may be implemented to manufacture a prosthetic or orthotic device for a patient's lower limb (e.g., a patient's leg), a patient's upper limb (e.g., a patient's arm), a patient's foot, a patient's hand, a head wearable orthotic, or any other prosthetic or orthotic configured to be worn by a patient.

Configuration of Exemplary Embodiments

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claim.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the systems as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claim.

What is claimed is:

1. A prosthetic assembly comprising:

a socket comprising a first interlocking feature, the socket defining an inner volume; and a liner comprising a second interlocking feature, wherein the first interlocking feature and the second interlocking feature are configured to engage each other when the liner is inserted into the inner volume of the socket, the liner configured to receive a distal limb of a patient;

wherein at least one of the socket or the liner comprise a plurality of inner voids extending within walls of the socket or the liner, wherein the plurality of inner voids comprise a first set of internal channels for heat dissipation from the patient's distal limb to facilitate cooling of the patient's distal limb, a second set of internal channels for moisture evaporation from the patient's distal limb to facilitate evaporation of sweat or bodily fluids from the patient's distal limb, and a third set of internal channels for electrical components, the third set of internal channels configured to receive at least one sensor or transducer and at least one myoelectric wire, wherein a portion of at least one of the plurality of inner voids includes a passageway extending along a first longitudinal length of the socket or the liner, the passageway defined by (1) a groove in the socket and (2) a groove in the liner, wherein the groove in the socket is aligned with the groove in the liner along a second longitudinal length of the socket or the liner.

2. The prosthetic assembly of claim 1, wherein the electrical components comprise components of a Peltier cooling system.

3. The prosthetic assembly of claim 1, wherein the plurality of inner voids comprise a fourth set of internal channels configured to provide therapy or medication to the patient's distal limb.

4. The prosthetic assembly of claim 1, wherein at least one of the socket or the liner comprises a variable thickness along a longitudinal length or radial direction of the socket or the liner.

5. The prosthetic assembly of claim 1, wherein the liner comprises a lattice structure, the lattice structure positioned at a distal end of the liner and positioned between a double wall of the liner, the lattice structure configured to facilitate desired transfer of forces between the prosthetic assembly and the patient's distal limb, to absorb impact forces, and to reduce shear stress.

6. The prosthetic assembly of claim 1, wherein the prosthetic assembly is an above-the-knee or below-the-knee lower limb prosthetic assembly.

7. The prosthetic assembly of claim 1, wherein the prosthetic assembly is an above-the-elbow, below-the-elbow, at the wrist, or a finger upper limb prosthetic assembly.

8. The prosthetic assembly of claim 1, wherein the socket is manufactured from a thermoplastic or a thermoplastic reinforced with carbon.

9. The prosthetic assembly of claim 1, wherein the liner is manufactured from a flexible silicone material or a rubber.

10. The prosthetic assembly of claim 1, wherein an exterior surface of the liner and an internal surface of the socket are configured to engage each other to define sealed vacuum sections between the liner and the socket, wherein other sections of the liner and the socket do not define sealed vacuum sections.

11. The prosthetic assembly of claim 1, wherein the prosthetic assembly is entirely manufactured through at least one of:

additive manufacturing; or injection molding.

12. The prosthetic assembly of claim 1, wherein at least one of the liner or the socket comprise connection points configured to couple additional componentry to the prosthetic assembly.

13. The prosthetic assembly of claim 12, wherein the connection points comprise an extrusion or a recess disposed on the liner or the socket.

14. The prosthetic assembly of claim 1, wherein the first interlocking feature comprises a protrusion and the second interlocking feature comprises a void, wherein the protrusion is configured to be received within the void to removably couple the socket with the liner.

15. The prosthetic assembly of claim 1, wherein the first interlocking feature comprises a void and the second interlocking feature comprises a protrusion, wherein the protrusion is configured to be received within the void to removably couple the socket with the liner.

16. The prosthetic assembly of claim 1, wherein the socket and the liner are configured to conform to an anatomical shape of the patient's distal limb.

17. The prosthetic assembly of claim 1, wherein the first set of internal channels or the second set of internal channels includes an outlet through an external surface of the socket.

18. A prosthetic assembly, comprising:

a socket comprising a first interlocking feature, the socket defining an inner volume; and a liner comprising a second interlocking feature, wherein the first interlocking feature and the second interlocking feature are configured to engage each other when the liner is inserted into the inner volume of the socket, the liner configured to receive a distal limb of a patient;

wherein at least one of the socket or the liner comprise a plurality of inner voids extending within walls of the socket or the liner;

wherein the first interlocking feature comprises a protrusion and the second interlocking feature comprises a void, wherein the protrusion is configured to be received within the void to removably couple the socket with the liner; and wherein a portion of at least one of the plurality of inner voids includes a passageway extending along a longitudinal length of the socket or the liner, the passageway defined by a groove in an internal surface of the socket and an external surface of the liner.

* * * * *